United States Patent
Ogle

(10) Patent No.: US 8,123,775 B2
(45) Date of Patent: Feb. 28, 2012

(54) EMBOLISM PROTECTION DEVICES

(75) Inventor: Matthew F. Ogle, Oronoco, MN (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 1257 days.

(21) Appl. No.: 10/806,311

(22) Filed: Mar. 22, 2004

(65) Prior Publication Data

US 2004/0220611 A1    Nov. 4, 2004

Related U.S. Application Data

(63) Continuation of application No. 10/414,909, filed on Apr. 16, 2003, now Pat. No. 7,303,575.

(60) Provisional application No. 60/400,341, filed on Aug. 1, 2002.

(51) Int. Cl.
*A61M 29/00* (2006.01)

(52) U.S. Cl. ........................... 606/200; 623/1.11

(58) Field of Classification Search .................. 428/131, 428/397; 606/108, 114, 194, 198, 200, 159
See application file for complete search history.

(56) References Cited

U.S. PATENT DOCUMENTS

| | | | |
|---|---|---|---|
| 4,422,939 A | 12/1983 | Sharp et al. | |
| 4,512,338 A | 4/1985 | Balko et al. | |
| 4,550,126 A | 10/1985 | Lorenz | |
| 4,793,348 A | 12/1988 | Palmaz | |
| 4,817,600 A | 4/1989 | Herms et al. | |
| 4,832,055 A | 5/1989 | Palestrant | |
| 5,059,205 A | 10/1991 | El-Nounou et al. | |
| 5,061,276 A * | 10/1991 | Tu et al. | 623/1.33 |
| 5,200,248 A * | 4/1993 | Thompson et al. | 428/131 |
| 5,277,976 A * | 1/1994 | Hogle et al. | 428/397 |
| 5,350,398 A | 9/1994 | Pavcnik et al. | |
| 5,370,657 A | 12/1994 | Irie | |
| 5,407,673 A | 4/1995 | Reich et al. | |
| 5,540,707 A | 7/1996 | Ressemann et al. | |
| 5,569,463 A | 10/1996 | Helmus et al. | |
| 5,651,765 A | 7/1997 | Haworth et al. | |
| 5,693,067 A * | 12/1997 | Purdy | 606/200 |
| 5,704,910 A | 1/1998 | Humes | |
| 5,720,764 A | 2/1998 | Naderlinger | |
| 5,782,791 A | 7/1998 | Peterson et al. | |
| 5,807,306 A | 9/1998 | Shapland et al. | |
| 5,810,874 A * | 9/1998 | Lefebvre | 606/200 |
| 5,836,868 A | 11/1998 | Ressemann et al. | |
| 5,836,962 A * | 11/1998 | Gianotti | 623/1.51 |

(Continued)

FOREIGN PATENT DOCUMENTS

EP    1226795 A2    7/2002

(Continued)

OTHER PUBLICATIONS

U.S. Appl. No. 10/414,909, filed Aug. 16, 2003, Ogle.

(Continued)

*Primary Examiner* — Victor X Nguyen

(57) ABSTRACT

Embolism protection devices can be formed with a biocompatible expandable polymer that can expand upon release within a patient's vessel. Upon release, the structure can be configured to filter flow through the vessel. The material of the embolism protection devices can release one or more biologically active agents, such as a thrombolitic agent, including, for example, tPA. Alternatively or additionally, the embolism protection device can be connected to a tether that elutes one or more biologically active agents.

18 Claims, 12 Drawing Sheets

U.S. PATENT DOCUMENTS

| | | | |
|---|---|---|---|
| 5,911,704 A | 6/1999 | Humes | |
| 5,914,125 A | 6/1999 | Andrews et al. | |
| 5,919,145 A | 7/1999 | Sahatjian | |
| 5,928,260 A * | 7/1999 | Chin et al. | 606/200 |
| 5,935,139 A | 8/1999 | Bates | |
| 5,938,645 A | 8/1999 | Gordon | |
| 5,941,869 A | 8/1999 | Patterson et al. | |
| 5,972,019 A | 10/1999 | Engelson et al. | |
| 5,972,505 A * | 10/1999 | Phillips et al. | 428/397 |
| 5,977,429 A | 11/1999 | Phillips et al. | |
| 6,001,118 A * | 12/1999 | Daniel et al. | 606/200 |
| 6,066,149 A | 5/2000 | Samson et al. | |
| 6,099,864 A | 8/2000 | Morrison et al. | |
| 6,103,376 A | 8/2000 | Phillips et al. | |
| 6,123,681 A | 9/2000 | Brown, III | |
| 6,160,084 A | 12/2000 | Langer et al. | |
| 6,231,589 B1 | 5/2001 | Wessman et al. | |
| 6,238,412 B1 | 5/2001 | Dubrul et al. | |
| 6,245,088 B1 | 6/2001 | Lowery | |
| 6,245,089 B1 | 6/2001 | Daniel et al. | |
| 6,254,563 B1 | 7/2001 | Macoviak et al. | |
| 6,267,776 B1 | 7/2001 | O'Connell | |
| 6,273,901 B1 | 8/2001 | Whitcher et al. | |
| 6,306,163 B1 | 10/2001 | Fitz | |
| 6,346,116 B1 | 2/2002 | Brooks et al. | |
| 6,364,895 B1 | 4/2002 | Greenhalgh | |
| 6,364,896 B1 | 4/2002 | Addis | |
| 6,368,338 B1 | 4/2002 | Konya et al. | |
| 6,368,344 B1 | 4/2002 | Fitz | |
| 6,371,969 B1 | 4/2002 | Tsugita et al. | |
| 6,371,970 B1 | 4/2002 | Khosravi et al. | |
| 6,391,044 B1 | 5/2002 | Yadav et al. | |
| 6,391,300 B1 | 5/2002 | Rose et al. | |
| 6,395,014 B1 * | 5/2002 | Macoviak et al. | 606/200 |
| 6,450,989 B2 | 9/2002 | Dubrul et al. | |
| 6,485,501 B1 | 11/2002 | Green | |
| 6,485,502 B2 | 11/2002 | Don Michael et al. | |
| 6,491,965 B1 | 12/2002 | Berry et al. | |
| 6,514,273 B1 | 2/2003 | Voss et al. | |
| 6,527,746 B1 | 3/2003 | Oslund et al. | |
| 6,602,271 B2 | 8/2003 | Adams et al. | |
| 6,605,111 B2 | 8/2003 | Bose et al. | |
| 6,610,077 B1 | 8/2003 | Hancock et al. | |
| 6,878,153 B2 | 4/2005 | Linder et al. | |
| 6,986,778 B2 | 1/2006 | Zadno-Azizi | |
| 7,052,500 B2 | 5/2006 | Bashiri et al. | |
| 2002/0062133 A1 | 5/2002 | Gilson et al. | |
| 2002/0072550 A1 | 6/2002 | Brady et al. | |
| 2002/0128680 A1 | 9/2002 | Pavlovic | |
| 2004/0093015 A1 | 5/2004 | Ogle | |
| 2004/0153118 A1 | 8/2004 | Clubb et al. | |
| 2005/0021075 A1 | 1/2005 | Bonnette et al. | |

FOREIGN PATENT DOCUMENTS

| | | |
|---|---|---|
| WO | WO 02/055146 | 7/2002 |

OTHER PUBLICATIONS

U.S. Appl. No. 10/781,503, filed Feb. 18, 2004, Ogle et al.

Fasseas et al., "Distal protection devices during percutaneous coronary and carotid interventions," current Controlled Trials in Cardiovascular Medicine, vol. 2, No. 6, Dec. 2002, 5 pages.

"Smart suture is first application of novel MIT polymer," from website http://web/mit.edu/newsoffice/nr/2002/langer-suture.html, Apr. 25, 2002, 3 pages.

Reichenspurner et al., "Particulate emboli capture by an intra-aortic filter device during cardia surgery," The Journal of Thoracic & Cardiovascular Surgery, vol. 119(2), Feb. 2000, pp. 233-241.

Harbinger et al., "Capture of particulate emboli during cardiac procedures in which aortic cross-clamp is used," The Society of Thoracic Surgeons, vol. 70, 2000, pp. 1119-1123.

4DG? Fibers; http://web.archive.org/web/2011030070010//http://fitfibers.com/4DG_Fibers.htm; (Oct. 30, 2001).

Fiber Innovative Technology: biocomponent and specialty fibers; FIT Capabilities; http://web.archive.org/web/20010217040848/http://www.fitfibers.com/capabilities.htm (Feb. 17, 2001).

Fiber Innovation Technology: biocomponent and specialty fibers; FIT Products; http://web.archieve.org/web/20010408003529/http://www.fitfibers.com/product.htm.

4DG? Fibers; http://web.archive.org/web/2011030070010//http://fitfibers.com/4DG_Fibers.htm; (Oct. 30, 2001).

Fiber Innovative Technology: biocomponent and specialty fibers; FIT Capabilities; http://web.archive.org/web/20010217040848/http://www.fitfibers.com/capabilities.htm (Feb. 17, 2001).

Fiber Innovation Technology: biocomponent and specialty fibers; FIT Products; http://web.archieve.org/web/20010408003529/http://www.fitfibers.com/product.htm.

* cited by examiner

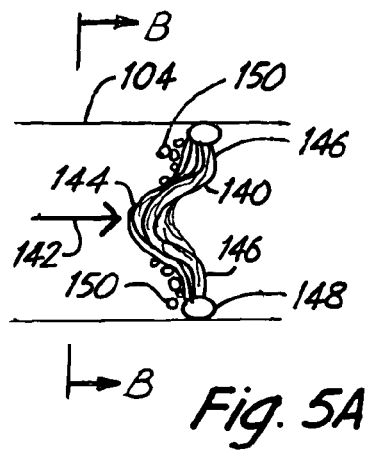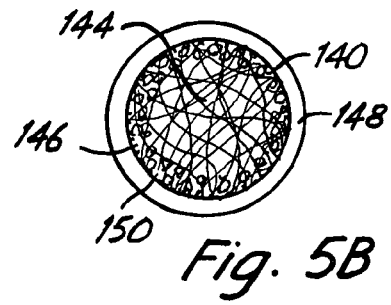
Fig. 5A    Fig. 5B
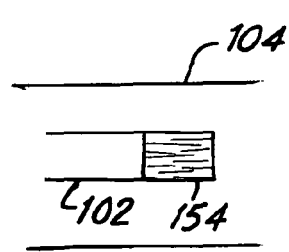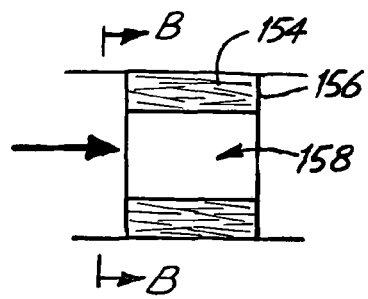
Fig. 6A
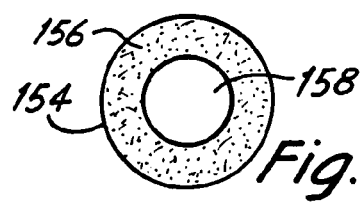
Fig. 6B
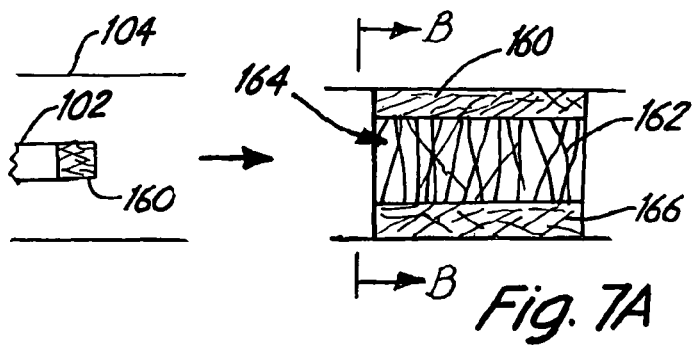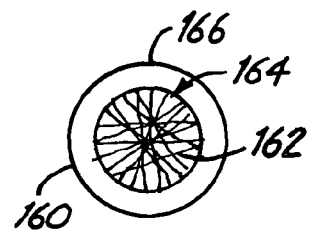
Fig. 7A    Fig. 7B

EMBOLISM PROTECTION DEVICES

CROSS REFERENCE TO RELATED APPLICATIONS

This application is a continuation of U.S. patent application Ser. No. 10/414,909, filed Apr. 16, 2003, now issued U.S. Pat. No. 7,303,575 to Ogle, entitled "Embolism Protection Devices, incorporated herein by reference, which claims priority to U.S. Provisional Patent Application Ser. No. 60/400,341, filed Aug. 1, 2002, to Ogle, entitled "Embolism Protection Device," incorporated herein by reference.

FIELD OF THE INVENTION

The invention relates to devices for preventing blockage of passageways in a patient's body. In particular, the invention relates to devices placed within a vessel, such as a blood vessel or a urinary vessel, to trap occlusions, such as emboli, for their dissolution or removal, as well as related methods.

BACKGROUND OF THE INVENTION

An embolus can be any particle comprising a foreign or native material, which enters the vascular system with potential to cause occlusion of blood flow. Emboli can be formed from aggregated fibrin, red blood cells, collagen, cholesterol, plaque, fat, calcified plaque, bubbles, arterial tissue, and/or other miscellaneous fragments. Emboli range in size from 0.01 cubic millimeters ($mm^3$) to 12.5 $mm^3$ (with an approximate mean of 0.80 $mm^3$). Emboli characterization is described further described in reference 1. (1) While some references are cited explicitly in the text, other references are cited in a list at the end of the specification. References listed at the end of the specification are cited with a number of the reference in parentheses. These references are incorporated by reference in their entirety as well as specifically for the particular principle being referenced.

Cardiac Surgery

Each year there are approximately 800,000 cardiac surgical cases which involve cardiopulmonary bypass (CPB) worldwide. (2) Of these cardiac surgical cases, approximately 48,000 suffer stroke and nearly 300,000 experience some neurocognitive disturbance. (3) This is a significant clinical problem. These complications are due in large measure to CPB-generated emboli. The average number of emboli measured by Trans Cranial Doppler (TCD) in patients undergoing cardiopulmonary bypass is 183 (range 3-947). (2) The majority of emboli end up in the very distal cerebral tree, the terminal arterioles and capillaries causing microinfarctions, (i.e., loss of blood to surrounding tissue). (4) Pathological evaluation of affected tissues reveals sausage-shaped arterial dilatations known as SCADs. Cerebral microinfarctions can cause confusion, disturbances of speech, paralysis, visual disturbances, balance disturbances and other neurological deviations. (5) These impairments are frequently short term but can be permanent.

Whether long term or short term, neurocognitive disturbances translate into significant patient care spending. An estimated $750 million dollars is spent annually on hospital care for CPB patients and an additional $500 million on long-term hospice care. (2) The average stay for CPB patients without adverse cerebral outcomes is 8.6 days, while patients with severe adverse outcomes stay an average of 55.8 days. (3 and 6) Estimating the average hospital day care cost at $1500/day, extended stays due to embolic events translate on average into an additional $60,000 per patient. While daunting, this figure still fails to include the social and financial burden placed on family members upon hospital release. In sum, surgically triggered embolic events cause high rates of clinically observed neurological disturbances, decreased quality of life and increased patient care spending.

Cardiac surgical procedures have been correlated directly with neurological injury and stroke due in large measure to the formation of emboli. Emboli can be generated by surgical maneuvers such as cannulation, aortic manipulation, clamping and unclamping. In fact, by some estimates, 60% of the total emboli can be associated with clamp manipulation alone. The average number of emboli measured by Trans Cranial Doppler (TCD) in patients undergoing coronary bypass is 135 (range 0-1377), and in patients undergoing vascular surgery, the average number increases to 1030 (range 18 to 5890). The majority of the emboli end up in the very distal cerebral tree, the terminal arterioles and capillaries causing microinfarcts, (i.e., loss of blood to surrounding tissue).

Furthermore, mortality increased from 7.4% in patients without adverse cerebral outcomes to 30.4% in patients who did have adverse cerebral outcomes. A study conducted in Sweden reviewed 7,000 open heart procedures. Their results with respect to incidence of symptoms as a percentage of all cases are as follows: disturbance of consciousness including slow awakening (1.8%), confusion (5.3%), disturbances of speech (1.3%), paresis (2.0%), visual disturbances (1.0%), balance/coordination disturbances (2.3%), seizures (0.2%) and other neurological deviations (1.8%).

Vascular Surgery

Emboli formation can also create problems in the realm of vascular disease, though in these instances the clinical outcome can be pulmonary embolism (PE). Approximately 600,000 people in the United States suffer from venous thrombi, which could result in a lung embolus. Mortality associated with untreated PE is approximately 30%. (7) While secondary to cardiac surgery, this area represents a Significant clinical indication.

Cardiology and Endovascular Intervention

Other procedures that can result in emboli include, for example, coronary, carotid, and peripheral interventions. (8) In these cases, particulate matter, including, for example, plaque, debris and thrombus, can form emboli distal to the site of intervention. As a result, blood flow to the distal vascular bed is diminished and periprocedural end-organ ischemia and infarction can result. Distal embolization of large particles produced at the time of such interventions as balloon inflation or stent deployment may obstruct large, epicardial vessels, and smaller particles (as little as 15-100 microns) can cause microinfarcts and/or myocardial infarctions and left ventricular dysfunction. (8) Myocardial infarction refers to the death of a section of myocardium or middle layer of the heart muscle. Myocardial infarction can result from at least partial blockage of the coronary artery or its branches. Blockage of capillaries associated with the coronary arteries can result in corresponding microinfarctions/microinfarcs.

Urology and Gastroenterology

Blockage of other body vessels can occur. For example, kidney stones are one of the most painful of the urologic disorders. Kidney stones also represent one of the most common disorders of the urinary tract; it is estimated that more than 1 million cases were diagnosed in 1996. It has also estimated 10 percent of people in the United States will have a kidney stone at some point in their lives. While most kidney stones pass out of the body without any intervention, stones that cause lasting symptoms or other complications require removal. Thus, like the other emboli generated in vascular system, urology could benefit from a devices to remove and resorb calculi in the urinary tract. This calculi is composed of calcium oxalate. Since it is a relatively hard substance, it can cause great pain as it passes through the urinary tract. Such removal is often necessary in cases of obstruction, i.e. embolism.

Emboli and Infection

When foreign material in the stream of flow causes turbulence or low flow, it has been shown that this increases infection rates. Thrombus not only generates emboli, but also increases the risk of infection. (9) Likewise kidney stones can create additional risk for infection.

It is evident that a wide variety of embolic events cause high rates of clinically observed symptoms, decreased quality of life and increased patient care spending.

SUMMARY OF THE INVENTION

In a first aspect, the invention pertains to an embolism protection device comprising a biocompatible expandable polymer. The expandable polymer can expand upon release within a patient's vessel into a structure configured to filter flow through the vessel. Corresponding methods relate to delivering an embolism protection device into a patient's vessel.

In another aspect, the invention pertains to an embolism protection device comprising a biocompatible resorbable polymer forming a porous structure having a configuration to filter flow through a patient's vessel.

In an additional aspect, the invention pertains to an embolism protection device comprising a polymer forming a porous structure and a biologically active agent that elutes from the device when the device is in contact with flow within a patient's vessel. The porous structure has a configuration to filter flow through the patient's vessel.

Moreover, the invention pertains to an embolism protection device comprising a first section and a compositionally distinct second section. The first section has a different average composition from the average composition of the second section. Also, the first section and the second section are configured for placement within a patient's vessel with a substantial fraction of flow passing sequentially through the first section and the second section.

Furthermore, the invention pertains to a system for providing protection from emboli comprising an embolic protection device and a delivery tool. The delivery tool is configured for releasing the embolism protection device into a vessel from the catheter. The embolism protection device comprises a biocompatible expandable polymer.

In addition, the invention pertains to a method for reducing or eliminating adverse effects of an embolus, the method comprises delivering an embolism protection device and administering a biologically active agent. The delivering of the embolism protection device can be performed within a vessel of a patient with the device being tethered with a tether such that the embolism protection device filters flow within the vessel. The administering of the biologically active agent can be performed through the tether.

In an additional aspect, the invention pertains to an embolism protection device comprising a plurality of fibers having surface capillaries. The fibers are bound within a structure and have a deployed configuration that fills the lumen of a vessel having a diameter corresponding to that of a human vessel. The fibers can include one or more surface capillary channels. The capillary channels within a single fiber are substantially parallel to each other, if there are multiple surface capillary channels, and substantially parallel to the length of the fiber. The capillary channels can have an open groove along at least about 20% of their length and generally along from about 90% to 100% of their length.

In a further aspect, the invention pertains to a system for trapping emboli comprising a delivery tool comprising a tether and an embolism protection device attached to the tether. The embolism protection device comprises a fiber with surface capillaries with a size suitable for placement within a human vessel.

In another aspect, the invention pertains to a method for trapping emboli, the method comprising placing a fiber within a patient's vessel wherein the fibers have surface capillaries.

BRIEF DESCRIPTION OF THE DRAWINGS

FIG. 5A is a schematic side view of an alternative embodiment of an embolism protection device within a patient's vessel following deployment.

FIG. 5B is an end on view of the device of FIG. 5A viewed along line B-B of FIG. 5A.

FIG. 6A is a schematic side view of an alternative embodiment of an embolism protection device within a patient's vessel with the left view showing the deployment of the device from a deployment apparatus and the right view showing the device following deployment.

FIG. 6B is an end on view of the device of FIG. 6A viewed along line B-B of FIG. 6A.

FIG. 7A is a schematic side view of an alternative embodiment of an embolism protection device within a patient's vessel with the left view showing the deployment of the device from a deployment apparatus and the right view showing the device following deployment.

FIG. 7B is an end on view of the device of FIG. 7A viewed along line B-B of FIG. 7A.

DESCRIPTION OF THE INVENTION

Figure 1:
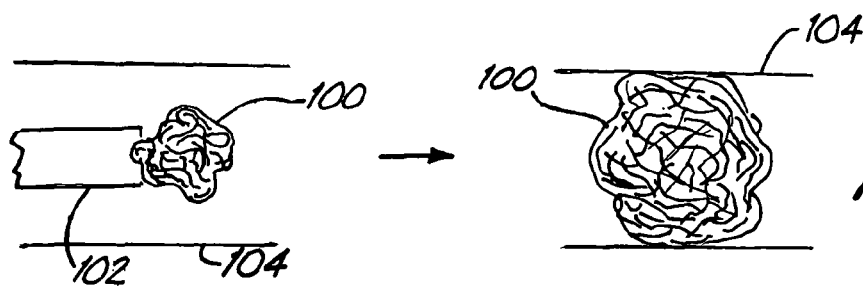
FIG. 1 is a schematic side view of an embolism protection device within a patient's vessel with the left view showing the deployment of the device from a deployment apparatus and the right view showing the device following deployment.

Improved medical devices to capture and/or remove/dissolve emboli and similar particles can incorporate a polymer that expands in an aqueous environment of the body. The emboli have the potential to occlude vessels to form an embolism in a patient. Suitable polymers include, for example, hydrogels and memory polymers that resume a memory shape upon exposure to a stimulus such as heating to body temperature. In some embodiments, the embolism protection device comprises a blend of polymers, such as a structural polymer that provides a framework for the device and a hydrogel. The blend of polymers can be in the form of a graft copolymer or the like. The devices can further comprise a bioactive agent, such as an agent that is effective to dissolve the emboli. Generally, the embolism protection device is removed following an appropriate period of time to effectively remove any emboli within the device. The embolism protection device generally is used to control emboli following a medical procedure.

An embolus as used herein refers broadly to a particle, besides living cells, in a vessel within a mammal having a diameter of at least about 5 microns. For this determination, the diameter is considered the largest distance between two points on the surface of the particle. Thus, emboli would encompass emboli within the blood as well as kidney stones and the like. Vascular emboli are thought to be composed almost exclusively of clotted blood. Arterial emboli generated in aortic surgery or endovascular intervention can be composed of other components, but it is generally believed that they nearly all contain some component of fibrin. See, for example, Reichenspumer et al., "Particulate emboli capture by an inter-aortic filter device during cardiac surgery," J. Thorac. Cardiovasc. Surg. 119(2):233-241 (February 2000), Harringer, "Capture of particulate emboli during cardiac procedures in which aortic cross-clamp is used," Ann. Thorac. Surg. 119(2):701119-23 (February 2000) and Webb, "Retrieval and analysis of particulate debris after saphenous vein graft intervention," J. American College Cardiol. 34(2): 468-475 (1999), all three of which are incorporated herein by reference. In some embodiments, embolism protection devices, described herein, can protect the patients in at least one of three ways: first by filtering emboli, second by dissolving entrapped emboli and third by bathing the distal myocardial bed or other down flow portion of a vessel with a beneficial bioactive agent, such as an embolism dissolving compound, for example, tissue plasminogen activator (tPA), to help resolve emboli which have become impacted there.

The embolism protection device can be delivered, for example, out of a medical implement (catheter or syringe) into the desired vessel, such as a vascular vessel. In some embodiments, the material of the device can swell/dilate quickly upon exposure to the aqueous environment of a patient's body to circumferentially encompass/fill the vessel. The expansion of the device can anchor the device within the vessel due to contact with the vessel wall. In some embodiments, the device can have the flexibility to conform to the geometry of the vessel. The materials and structure of the device can be selected to have porosity that would allow blood elements, such as white blood cells (about 7-20 microns), red blood cells (8-9 microns) and platelets (2-4 microns), yet collects emboli. In contrast, emboli generally range in size with diameters from about 20 microns to about 3.5 mm, in some embodiments from about 45 microns to about 1000 microns and in further embodiments from about 50 microns to 200 microns. A person of ordinary skill in the art will recognize that additional ranges of emboli within the explicit ranges are contemplated and are within the present disclosure. Thus, in some embodiments of interest, the trapping of emboli with a size larger than about 45 microns to about 50 microns would be beneficial.

In some embodiments of particular interest, an embolism protection device can comprise a polymeric substrate (media, sponge), especially an expandable polymer, such as a swelling polymer, a memory polymer or a compressed polymer. Specifically, in some embodiments, the embolism protection devices described herein generally comprise a swelling polymer that expands, generally spontaneously, upon contact with an aqueous solution, such as blood or other body fluids. Swelling is considered broadly in terms of significant changes in dimension due to an absorption or other intake of fluid/liquid into the structure of the material, such as with a sponge, a hydrogel or the like. Hydrogels are generally hydrophylic polymers that are nevertheless not soluble in aqueous solutions. Generally, hydrogels are crosslinked to prevent them from being soluble. While they do not dissolve, the hydrogels swell with aqueous solution when in contact with the solution due to the hydrophylic nature of the polymer. In additional or alternative embodiments, an expandable polymer can comprises a memory polymer that resumes a memory shape upon exposure to a stimulus, such as exposure to body temperature. In other embodiments, the expandable polymer can comprise a compressible polymer that expands upon release of a confining force such as the confinement provided by a sheath or the like. Furthermore, the embolism protection device can comprise additional polymers and/or other material to introduce desired properties to the device.

Thus, in some embodiments of interest, the devices have a component of an expandable polymer to fill the inner luminal space of the vessel. In addition, copolymers and/or polymer blends can be used in which one or more expandable polymers is combined with other monomer and/or polymer moieties to combine the properties of the different elements. For example, block copolymers, such as graft copolymers, can be used to combine polymer units into a combined material that incorporates properties of the respective polymers. Some embodiments of swelling polymers include, for example, hydrogels, which can expand large amounts upon contact with aqueous solutions. Various hydrogels suitable for medical applications are known in the art, and particular embodiments are described further below.

Additional polymers, such as polyesters, polyurethanes, modified polyurethanes, and polycarbonates, within a copolymer or a polymer blend can provide mechanical strength to the composite material. The embolism protection device can comprise one or more additional materials, as desired, to provide particular structural or functional features. For example, the outer surface can comprise a material, such as an adhesive or a fabric that expands with the material but contributes to anchoring of the device to the wall of the vessel. Some embodiments could contain multiple materials for modifying the composition and/or the structure, as desired.

With appropriate sizing, the embolism protection device can be applied to any size vessel of a patient. The patient can be any animal, generally a mammal, with particular interest in humans, farm animals and other domestic animals. The devices generally have an ability to conform to irregularly shaped portions of a vessel. Thus, this invention could be used for a vascular surgery to prevent a clot, which could cause paralysis, amputation, surgical vascular intervention, other neurological impairment or death. Due to complications from emboli, such as a thrombus, there is a significant clinical need for an effective protection from emboli and resulting embolisms. For example, significant potential applications pertain to coronary intervention following Acute Myocardial Infarct (AMI). These cases can represent 25% of all coronary interventions (as reported at GW Stone Lennox Hill Hospital) due in large part to the commonly thrombus-laden lesions found in AMI patients. Due to the flexibility of some embodiments of devices described herein and the speed at which they can be applied, an embolism protection device can be applied in a wide range of circumstances. In cases such as a broken hip, deployment of the embolism protection device could be pre-formed as an emergency procedure to prevent clot formation for patient's with pro thrombotic disease which are known to clot. While the focus of the discussion herein focuses on material within blood vessels and the like, there is also interest in and prevention of occlusion of other biological vessels in a patient. In particular, the embolism protection device can be used in other vessels of a patient, such as urinary tract vessels.

In some embodiments, a biologically active agent can be released by way of the embolism protection device. For example, the biologically active agent can be released from a reservoir within the embolism protection device either quickly and/or in a gradual fashion. Additionally or alternatively, the embolism protection device can be connected during a procedure to an external source of biologically active agent that is released in a desired dose at or near the embolism protection device. For embodiments in which the embolism protection device comprises a reservoir of biologically active agents, the embolism protection device can also elute a biologically active agent from one or more materials, which could aid in neurological/vascular disease prevention associated with surgical. In some embodiments, the reservoir of biologically active agent is physically trapped within the material such that it is released quickly by expansion of the material upon delivery of the device. In other embodiments, the biologically active agent is eluted gradually by diffusion out from the material in which it is embedded or released gradually by degradation of the material. In some embodiments, the embolism protection device remains connected to a wire following delivery in which the wire has a small inner lumen through which the biologically active agent is delivered. The delivery through the wire can be at a controlled time and rate, for example, with a syringe, peristaltic pump or the like.

Some embodiments have one or more emboli dissolving agents released locally to reduce the emboli. These agents can be thrombolytic agents such as tissue plasminogen activator (tPA) or urokinase, or the agents can release mild acid (possibly along with a neutralizing base, such as bicarbonate) or anti-calcification enzymes such as osteopontin to resorb calcific plaque. In other embodiments, the devices can release $O_2$ and/or sugars to nourish the patient's brain cells. In other embodiments, the device can release vasodilators such as NO or heparin to increase the available $O_2$ transport. In other embodiments, the device can release growth factor, which could improve healing or create new vessels. In further embodiments, the device can release viral vectors, which transfected the surrounding cell to up regulate the release a polypeptide compound for extended therapy (e.g., tPA). Specifically, for protein/polypeptide based agents, the delivery of a gene (nucleic acid) encoding the agent in a vector, such as a viral vector, to promote in vivo expression of the protein is an alternative to the delivery of the protein itself. Delivery of vectors for desired polypeptides is described further below. The device similarly can be designed to release a plurality of these agents.

In some embodiments, the material of the device or a portion thereof can be selected to slowly resorb over time. In these embodiments, the device can be left within the patient rather than being removed. In some embodiments, even if a portion of the resorbable material were to dislodge from the aggregated material of the device, the resorbable material can still have the same porosity thus be able to filter while providing flow further up the vascular tree. Resorbable materials within the embolism protection device could be tuned to dissolve over a time range from a very short time to a very long time after surgery, as desired. In some embodiments; an imaging approach can determine the presence of calcified plaque trapped within the embolism protection device, which would then be removed surgically. In some embodiments a string/tether can be attached to the device for extraction of the device. This attachment can act to reduce the luminal size of the device upon extraction for some embodiments of the device. In some embodiments, an extraction device, such as a gripper or the like, can be used to facilitate the removal of the embolism protection device by physically compressing the embolism protection device.

Thus, the embolism protection devices described herein can be effective to reduce or eliminate damage resulting from emboli in circumstances in which potential damage may be indicated by the performance of particular medical procedure, from the identification of diseases and/or by injuries to the patient. The material properties of the device provide great flexibility in the design of the device with respect to different potential ways of handling the emboli. Through the use of swellable/expandable polymers, the devices can be very versatile with respect to convenience of delivery, conformability to a wide range of vessels and uniform performance in a range of environments. By combining biologically active agents with the devices, the improved structural features can be combined with the ability to deliver treatments to a localized environment.

Embolism Protection Device Structures

The embolism protection devices can have various sizes and shapes both with respect to the exterior surface before and after deployment and with respect to the arrangement of the materials through the cross section of the structure. The shape of the exterior of the device can influence the nature of the deployment, removal and/or performance of the device. The nature of the arrangement of the material across the device generally is formulated to be consistent with the maintenance of flow through the device while capturing emboli over an appropriate size such that they do not flow past the device.

With respect to the shape of the exterior of the device, this shape can be, for example, generally spherical, cylindrical, concave, or saddle shaped. A generally spherical or other shaped device may nevertheless have a roughly irregular surface contour about an average overall shape, which can orient and adjust to the vessel inside wall upon expansion. Some representative examples are provided below. Any particular device generally can conform to the size and shape of the inside of the vessel. While the particular device size depends on the size of the particular vessel, an embolism protection device following expansion within the vessel of a human patient general can have a diameter perpendicular to the flow direction from about 50 microns to about 35 millimeters (mm), in additional embodiments from about 100 microns to about 9 mm and in further embodiments, from about 500 microns to about 7 mm. A person of ordinary skill in the art will recognize that additional ranges of device diameters within the explicit ranges are contemplated and are within the present disclosure.

The texture of the outer surface can reflect the structure of the interior of the device, or the texture of the exterior of the device can be altered to provide a particular surface texture. For example, the surface of the device may be porous to reflect the porosity of the device generally to the flow. Alternatively, the surface can be treated to alter the texture and/or covered with a material, such as a fabric, to present an alternative surface contacting the inner surface of the vessel. For example, a fabric cover over the exterior can improve the gripping of the vessels interior surface without damaging the vessel wall. Suitable biocompatible fabrics can be used, such as those formed from polyesters.

Once the embolism protection device is positioned within a vessel, appropriate flow should be maintained through the device while emboli are trapped. Thus, with respect to the flow direction, the device has controlled porosity. This controlled porosity can be established by the nature of the material and/or by the particular structure. Specifically, the polymer density and composition within the device can lead to a distribution of pores such that desired flow is provided while emboli are trapped by the lack of pores with a diameter large enough for the emboli to pass. In some embodiments, the device comprises a composite of two structures/materials with different pore sizes from each other. For example, the device can comprise a first material with an average pore size following expansion of the device between about 150 microns and 300 microns to be positioned approximately downstream and a second material with an average pore size of about 50 microns to be positioned approximately upstream. Alternatively or additionally, the polymers can be specifically arranged to have a structure that directly leads to pore sizes with desired sizes one the device expands within the vessel. For example, the polymer can form tubes with selected diameters that orient along flow direction of the vessel, as described further below.

In general, the desired filtering properties and corresponding average pore sizes and pore size distributions of an embolism protection device may depend on the particular location of the particular vessel in which it is delivered. However, for many applications it can be desirable to block the flow of a substantial majority of particulates with a diameter of at least about 0.2 mm while allowing the flow of a substantial majority of particulates with a diameter of no more than about 0.001 mm, and in other embodiments, to block the flow of a substantial majority of particulates with a diameter of at least about 0.1 mm while allowing the flow of a substantial majority of particulates with a diameter of no more than about 0.01 mm. A person of ordinary skill in the art will recognize that additional ranges of filtering ability within the explicit ranges are contemplated and are within the present disclosure. A substantial majority of particulates can be considered to be at least about 99 percent.

In some embodiments, it is desirable to remove the embolism protection device at some period of time following deployment. Since the embolism protection device expands to contact the interior of the vessel walls, it may be desirable to introduce structures that facilitate the removal of the device. For example, the device can comprise one or more tubes, sheaths, rigid extensions, wires, strings, filaments, tethers or the like appropriately positioned for extracting the device. In some embodiments, the strings are placed such that pulling on the string tends to contract the device to reduce or eliminate friction on the vessel wall. For example, the strings can be positioned at or near the outer edge of the device that contacts the vessel wall such that pulling on the string tends to pull the exterior of the device toward the center of the vessel. Tethers and the like also can be useful to maintain an embolism protection device at a delivered position within a vessel. Thus, with a tether or guide wire to maintain the position of the embolism protection device against flow within the vessel, the device may or may not exert significant force against the inner wall of the vessel.

In addition, an extractor device can be positioned with a catheter or the like near the embolism protection device. For example, the extractor can comprise a gripping element that grips the device to reduce its dimensions by physical force such that the embolism protection device can be removed through a catheter or the like. A specific embodiment of a gripping device is described in the examples. Similarly, an extractor can comprise a sheath or the like. The embolism protection device can be tapered such that an end of the expanded device fits within the sheath. Then, pulling the device relative to the sheath, such as using a tether or the like, can compress the device within the sheath for removal of the device within the sheath from the patient. Similarly, the device can be twisted in a cork-screw type fashion to decrease the diameter of the device due to the torque and the compressible nature of the polymers. Similar approaches can be used for placement of the devices within a sheath for delivery of the device. For embodiments of embolism protection devices intended for removal from the patient, it may be desirable to have a smaller porosity toward the vessel wall relative to the porosity away from the vessel wall to reduce the possibility of emboli escaping from the device during the removal of the device from the patient. A specific embodiment with this structure is described further in the examples below.

Figure 2:
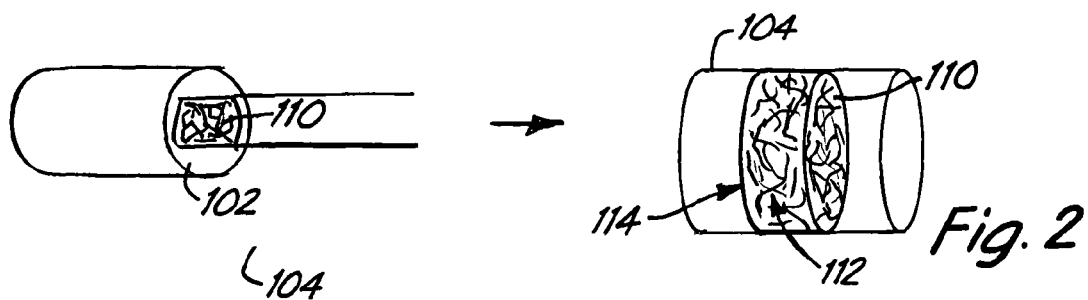
FIG. 2 is a schematic perspective view of an alternative embodiment of an embolism protection device within a patient's vessel with the left view showing the deployment of the device from a deployment apparatus and the right view showing the device following deployment.
Figure 3:
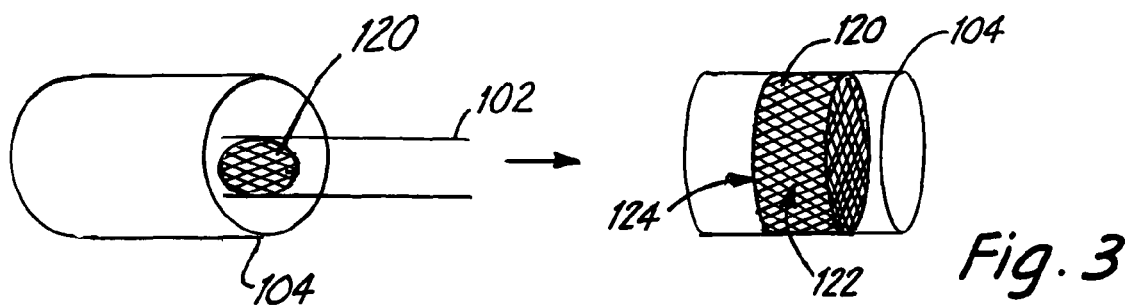
FIG. 3 is a schematic perspective view of another alternative embodiment of an embolism protection device within a patient's vessel with the left view showing the deployment of the device from a deployment apparatus and the right view showing the device following deployment.

Referring to FIG. 1, the left view displays an amorphous, generally spherical embolism protection device 100 adjacent a catheter 102 within a vessel 104. The right hand view in FIG. 1 shows device 100 following expansion to fill the lumen of vessel 104. The arrow indicates a temporal advance over which device 100 swells across the lumen of vessel 104. In this embodiment, device 100 has a random array of fibrous polymer forming the interior of the device 100. In an alternative embodiment, embolism protection device 110 has a cylindrical shape with a random interior polymer structure 112, as shown in FIG. 2. In this embodiment, device 110 has an outer surface covered with a fabric 114 excluding the flow ends through which the flow of the vessel passes. Referring to further alternative embodiment in FIG. 3, embolism protection device 120 has a generally cylindrical shape with a polymer matrix 122 that is approximately arranged on a grid. The outer surface of the cylinder is covered with fabric 124 with the ends of the cylinder exposed, i.e., free of the fabric. If fabric 124 has a sufficiently open weave, the fabric may also cover the ends of the cylindrical structure.

Figure 4:
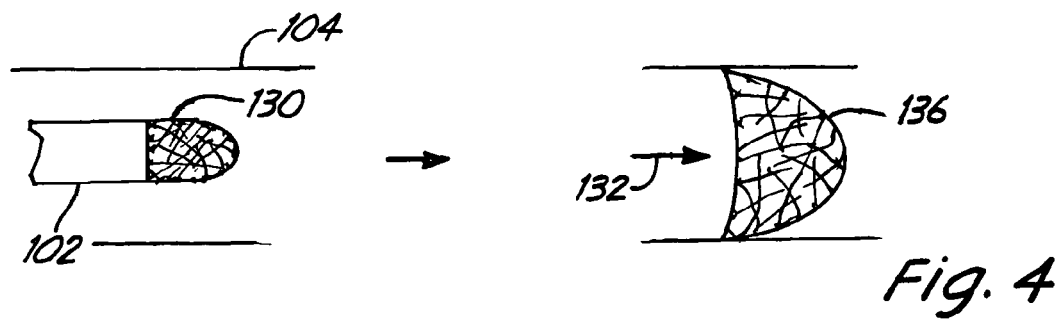
FIG. 4 is a schematic side view of another alternative embodiment of an embolism protection device within a patient's vessel with the left view showing the deployment of the device from a deployment apparatus and the right view showing the device following deployment.

As noted above, the embolism protection device can have a concave shape along the direction of the flow. Referring to FIG. 4, embolism protection device 130 has a generally bullet shape with the fluid flow oriented along arrow 132. Device 130 may or may not have a hollowed out interior along the concave surface. A saddle shaped embolism protection device 140 is shown in FIGS. 5A and 5B. In the side view of FIG. 5A, the direction of fluid flow is indicated by arrow 142. Device 140 has a convex central portion 144 with an outer collection portion 146. In this embodiment, device 140 has a cuff 148, which for example can be formed from rolled fabric or other polymer material, for contacting the wall of vessel 104. Force from the flow tends to force emboli 150 away from central portion 144 toward outer portion 146. An end view is shown in FIG. 5B. A bioactive agent, such as an thrombolytic agent, can be located at outer portion 146 for concentration at the location of emboli.

Referring to FIGS. 6A and 6B, embolism protection device 154 has an expandable outer section 156 that forms a hole 158 in the center upon expansion. This embodiment generally is intended to trap a larger embolism. While it is possible to design device 154 to provide some flow through outer section 156, generally this device is removed shortly following the capture of a larger embolism since flow can be significantly reduced due to the embolism. A variation on this embodiment is shown in FIGS. 7A and 7B. In this embodiment, embolism protection device 160 has polymer elements 162 that extend through a central core 164 within an outer ring 166. Polymer elements 162 create a filter that traps larger elements from the flow. Polymer elements may or may not swell upon contact with an aqueous solution, although outer ring 166 swell to expand to the wall of vessel 104.

Figure 8A:
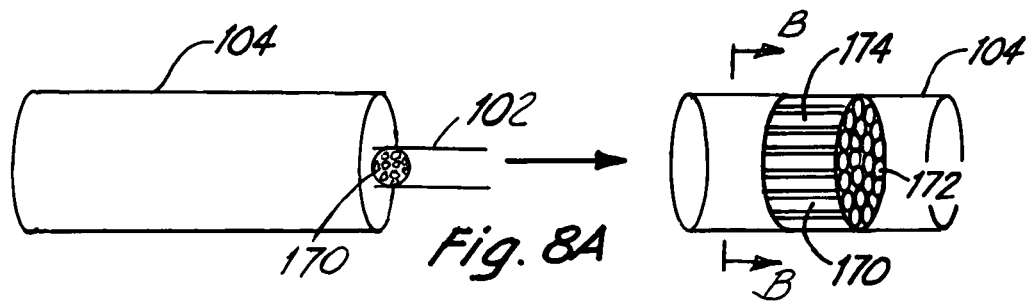
FIG. 8A is a schematic perspective view of an alternative embodiment of an embolism protection device within a patient's vessel with the left view showing the deployment of the device from a deployment apparatus and the right view showing the device following deployment.
Figure 8B:
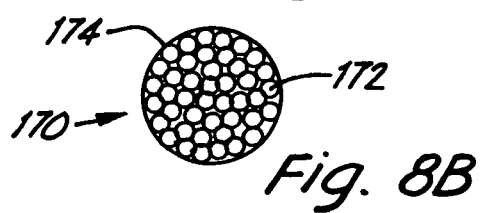
FIG. 8B is an end on view of the device of FIG. 8A viewed along line B-B of FIG. 8A.

Referring to FIGS. 8A and 8B, embolism protection device 170 has a plurality of tubular shaped passages 172 along the length of the generally cylindrical device. The outer cylindrical surface 174 may or may not be covered in a fabric. Furthermore, the tubular shaped passages 172 can be formed from a collection of polymer tubes assembled together to form the structure or from tubular openings through a polymer matrix.

Figure 9:
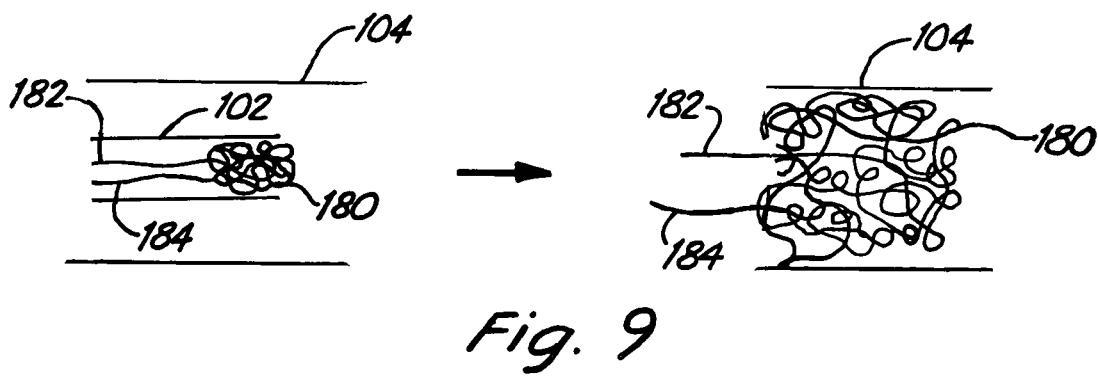
FIG. 9 is a schematic side view of an alternative embodiment of an embolism protection device with a tether to facilitate removal within a patient's vessel with the left view showing the deployment of the device from a deployment apparatus and the right view showing the device following deployment.
Figure 10:
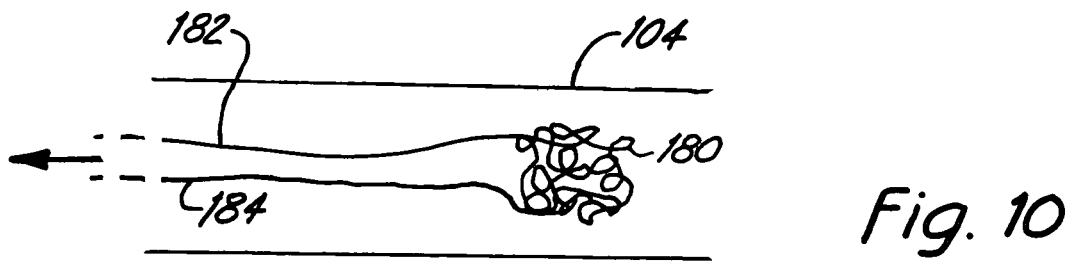
FIG. 10 is a schematic side view showing the use of the tether to remove the device of FIG. 9.

As noted above, an embolism protection device as described herein can comprise a tether or the like to facilitate removal of the device after sufficient time to protect against emboli. Referring to FIG. 9, embolism protection device 180 comprises two strings 182, 184 that tether device 180, although a single string or greater than two strings can be used. Device 180 is shown in an unexpanded configuration in the left wide of FIG. 9 and in its expanded form in the right side of FIG. 9. By providing two strings, pulling on the strings tends to draw the strings together to contract the device if the strings are in a spaced apart attachment on the device. As shown in FIG. 10, tension on strings 182, 184, as indicated by arrow 186, is resulting in contraction in diameter of device 180 and corresponding movement from right to left. Other configurations of strings can be used to tether an embolism protection device to facilitate removal and to contract the device, which may depend on the particular shape and structure of the device.

The embolism protection devices can comprise a composite of different structures, materials and/or bioactive agents. In particular, in these embodiments, the embolism protection device can have identifiable portions that are compositionally distinct with respect to the average composition within the portion. In some embodiments, the portions are positioned such that the flow or a substantial fraction of the flow passes sequentially through one section followed by another section. In such a configuration, generally at least about 25% of the flow volume and in other embodiments at least about 80% of the flow volume flow sequentially through the first portion followed by the second portion. A person of ordinary skill in the art will recognize that additional ranges of flow within the explicit ranges are contemplated and are within the present disclosure.

Figure 11:
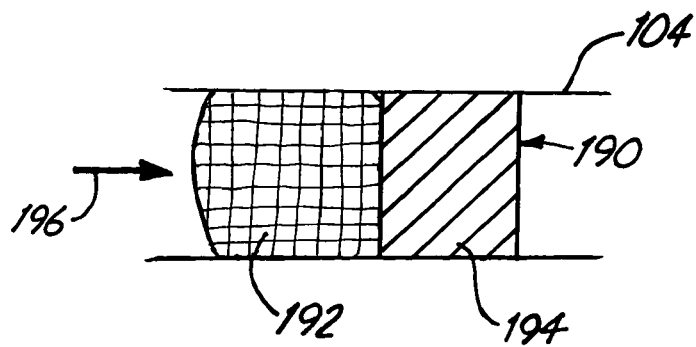
FIG. 11 is a schematic side view of an embolism protection device with two portions having different properties.

For example, as shown in FIG. 11, embolism protection device 190 comprises an up-flow portion 192 and a down-flow portion 194, where flow through the vessel is indicated with arrow 196. In some embodiments, up-flow portion 192 can elute, for example, a weak acid that tends to dissolve at least some emboli, while down-flow portion 194 can comprise a buffer that neutralizes the weak acid as it flows downstream.

In some embodiments, up-flow portion 192 and down-flow portion 194 can be separable. Thus, for example, up-flow portion 192 can provide a mesh, a sponge-like material and/or another porous material across the flow to collect emboli for subsequent removal. Down-flow portion 194 can be a tubular structure that does not significantly alter the flow, but elutes a bioactive agent, such as tPA and/or NO. Since the portions separate, up-flow portion 192 can be taken from the vessel to remove the trapped emboli while down-flow portion remains in the vessel to elute beneficial agents. In alternative embodiments, the positions of the two portions can be reversed with respect to the flow and the portion to be removed, i.e., the down-stream portion can be removed to leave the up-stream portion. In variations on this embodiment, the down-flow portion can also trap emboli. Thus, following the removal of the up-flow portion, the down-flow portion can be effective to trap emboli. The down-flow portion can be formed from a bioresorbable material such that it dissolves at a desired rate.

The structures in FIGS. 1-11 are representative structures for the embolism protection device. Additional structures can be formed based on the disclosure herein.

In some embodiments, the embolism protection devices can be distributed along with other components that can be used along with other instruments that facilitate the use of the embolism protection device. For example, an embolism protection device can be distributed along with delivery tools, retraction devices, tools for the delivery of biologically active agents, instructions and other suitable tools. Suitable delivery tools include, for example, sheaths and/or cannula into which the embolism protection device can be placed for delivery along with other catheter components that can facilitate the delivery of the device. Suitable retraction devices that facilitate the removal of the embolism protection device are described herein, which can be distributed with the embolism protection device. For the delivery of a biologically active agent along with the embolism protection device, a guide-wire with a hollow core and/or a cannulated syringe can be distributed with the embolism protection device. The cannulated syringe can be connected to the guide-wire for the delivery of a biologically active agent in the vicinity of the embolism protection device within the patient's vessel. The guide-wire may or may not be associated with the embolism protection device as a tether. In addition, the embolism protection device can be distributed with instructions, which can take to form of written instructions and/or electronic copies, including, for example, a direction to a suitable web site. The commonly distributed elements can be distributed in one or more containers, for example, as a kit. While the embolism protection device generally is disposable following removal from the patient, the other individual elements distributed with the embolism protection device may or may not be reusable following sterilization.

Materials

The embolism protection device can be fabricated from biocompatible materials, which can be delivered in vivo with limited vessel trauma, and, in some embodiments, can possess the ability to break down entrapped emboli. Some materials comprise a matrix, which can be capable in some embodiments of expanding upon delivery, capable of withstanding in vivo pressures to minimize movement and/or capable of delivering thrombolytic agents in a controlled fashion. The embolism protection devices described herein generally comprise one or more polymers with generally at least one polymer being an expandable polymer, e.g., swelling, shape adjusting and/or compressed, upon release in a vessel in a patient's body. Various suitable polymers can be used for swelling including, for example, highly absorbing hydrophilic polymers (e.g., polyether-polyurethane) or hydrogels, while shape adjusting polymers can be memory polymers as described below. Compressed polymers are physically deformable or elastic such that they can be squeezed into a sheath or the like for delivery into a vessel of the patient, such that the polymer expands following removal from the sheath. In some embodiments, the device comprises a plurality of polymers in a blend and/or a plurality of monomers in a copolymer, which can be a block copolymer. An advantage of using a plurality of polymers includes, for example, the ability to introduce properties characteristic of each individual polymer or of each monomer group incorporated into a copolymer.

In general, the expansion of the polymer and the corresponding device can occur spontaneously following the application of an appropriate stimulus. The appropriate stimulus can be, for example, contact with an aqueous fluid, release of constraining forces, such as applied by a sheath, and/or heating to body temperature. The expandable nature of at least some of the materials of the embolism protection devices inherently allows them to conform to the patient's vessel. Thus, minor variation in the vessel size and shape along the extent of the device can be handled appropriately by minor variations in the expansion of the device at different locations. However, for vessel or branch points of vessels that have a more complex non-cylindrical structure, the device shape can be formed specifically to adjust for delivery at the particular shape of the vessel. In these embodiments, the device expands into a predictable non-cylindrical shape due to the pre-shaping of the device.

Suitable swelling polymers can include, for example, hydrogels and sponge materials. The amount of swelling that takes place upon contact with an aqueous medium can range from about 10 percent to greater than a factor of twenty times (i.e. 2000 percent), in some embodiments from a factor of fifty percent to a factor of fifteen times, in other embodiments from a factor of two times to a factor of twelve times, and in further embodiments from a factor of seven times to a factor of ten times. A person of ordinary skill in the art will recognize that addition ranges of swelling within the explicit ranges are contemplated and are within the present disclosure. The desired degree of swelling may be selected to provide the desired degree of pressure between the device and the vessel wall following deployment as well as accounting for the relative sizes of the vessel and the delivery device, such as a catheter. The device may further be compressible apart from the expansion from hydration such that release of the device from the delivery system results in an expanded device relative to its pre-delivery size. However, generally some swelling or other expansion is used to maintain the device within the vessel in which the swelling provides pressure against the vessel wall. Generally, the device contacts the wall over a significant portion of its outer surface such that the force against the vessel is distributed over a significant area. Since the force generally is spread over a significant area, the magnitude of the force can be correspondingly reduced such that there is less potential for damage to the vessel wall. Furthermore, as described above, the embolism protection device can be tethered in place such that little or no force is needed between the device and the vessel wall to hold the device at the delivered position.

Hydrogels are hydrophylic polymers that generally are crosslinked to make them insoluble in an aqueous solution. Due to the hydrophylic nature of the polymer functional groups, the hydrogels draw aqueous solution into the polymer material. Suitable hydrogels include, for example, crosslinked forms of polyacrylamide, poly(hydroxyethyl-methacrylate) (PHEMA), cellulose derivatives, poly(vinyl alcohol) and polyethylene glycol. The degree of crosslinking, composition and other features can be used to control the degree of swelling. Some hydrogels can swell by a factor of 1000 percent or more upon contact with an aqueous solution. Several qualities of hydrogels have made them an attractive option in the medical device arena. These qualities include their ability to work as a protective barrier for open wounds and absorb excess fluids. In addition, hydrogels are biocompatible, nontoxic, and nonthrombogenic, have inherent adhesiveness to tissue and have been shown to deliver drugs in a controlled fashion. (15) Also, the hydrogels can be used to associate with other polymers that are less biocompatible or more thrombogenic to introduce desirable properties to the composite.

Suitable foam and sponge materials include, for example, polyester, aromatic vinyl polymers, polyether, polyurethane and mixtures thereof. Modified polyurethane polymers can be used to improve the biocomatability of the polymer. See, for example, U.S. Pat. No. 6,320,011 to Levy et al., entitled "Derivatized Polyurethane Compositions Which Exhibit Enhanced Stability In Biological Systems And Methods Of Making The Same," incorporated herein by reference. The foam/sponge materials can be formed, for example, in a molding process with a blowing agent. An example of a polymeric sponge material and methods of forming the sponge material are described further in U.S. Pat. No. 4,456,706 to Siedenstrang et al., entitled "Molding compounds, Sponge Articles Produced Therefrom And Process Of Production," incorporated herein by reference.

Compressible biocompatible polymers include, for example, foam products useful for biological applications. For example, hydrophilic polyether-polyurethanes and polycarboxylate polyurethanes can be used to form foam that are compressible while absorbing a large amount of aqueous solutions. U.S. Pat. No. 5,914,125 to Andrews et al., entitled "Wound Dressing," incorporated herein by reference, describes a hydrophilic polyether polyurethane foam material with an adsorptive capacity of at least about 10 times its own weight. In addition, published U.S. patent application Ser. No. 2002/0072550A to Brady et al., entitled "Biostable Polyurethane Products," incorporated herein by reference, describes foam materials with a void volume of 85% that are formed from either polyether polyurethanes or polycarbonate polyurethanes. In addition, polyurethanes poly-vinyl polymers can also be used to form biocompatible foams. U.S. Pat. No. 4,550,126 to Lorenz et al., entitled "Hydrophilic, Flexible, Open Cell Polyurethane-poly(N-vinyl lactam) Interpolymer Foam And Dental And Biomedical Products Fabricated Therefrom," incorporated herein by reference, describes a foam with a good ability to absorb aqueous fluids. These foams can be formed into appropriate shapes for use in the embolism protection devices described herein.

In some embodiments, the embolism protection device can comprise a polymer blend and/or copolymer as other polymers alone may not provide all desired functions or properties. Specifically, it may be desirable to use at least one polymer to provide additional mechanical strength to the device within the flow and an expanding polymer, such as a hydrogel, to introduce the expansion of the device upon delivery and to provide for control of the porosity of the expanded device. Suitable structural, biocompatible polymers for these blends include, for example, polyesters, such as polyethylene terephthalate, and polyurethanes, such as polycarbonate-polyurethanes, polyether polyurethanes, silicon-polyether-urethanes and silicon-polycarbonate-urethanes. For embodiments in which the expansion involves a swelling polymer, these polymer blends comprises from about 25 weight percent to about 95 weight percent structural polymer relative to the total polymer of the blends, and in further embodiments from about 35 to about 85 weight percent structural polymer relative to the total polymer of the blends. In embodiments in which expansion involves a shape changing polymer and/or a compresses polymer, a polymer blend generally would comprise at least about 40 weight percent expanding polymer and in other embodiments at least about 50 weight percent expanding polymer. Similarly, the proportions can be considered with respect to the weight of blocks of a block copolymer. A person of ordinary skill in the art will recognize that additional ranges of structural polymer proportions within the explicit ranges are contemplated and are within the present disclosure.

In some embodiments, the embolism protection device can comprise a biodegradable shape adjusting or memory polymer. These polymer can transition to a memory shape upon application of a stimulus, such as a temperature change. In particular, biodegradable polymers are available that resume a memory shape upon placement at body temperature or pH. The memory shape can be an expanded form that would extend the device across the lumen of the vessel. Thus, the memory polymer can expand the embolism protection device without the assistance of a swelling polymer, although the device may or may not comprise a blend or copolymer with the memory polymer and a hydrogel or other swelling polymer. Suitable memory polymers are described further in U.S. Pat. No. 6,160,084 to Langer et al., entitled "Biodegradable Shape Memory Polymers," incorporated herein by reference. These polymers, in particular, can be used to form devices with a saddle shape, as shown in FIGS. 5A and 5B. In some embodiments, the device with a biodegradable polymer can be combined with an initial amount of tPA and vectors to deliver an expressible tPA gene to transfect nearby cell to supply tPA on a longer term basis after the initial tPA with the device has eluted. The degradation of the device avoids the need to eventually remove the device and the supplies of tPA dissolve emboli such that the device does not become clogged with emboli during a more extensive implantation.

Other suitable memory polymers include, for example, hydrophilic polymer fibers, including, for example, polyester fibers. Suitable fibers are described, for example, in U.S. Pat. No. 5,200,248 to Thompson et al., entitled "Open Capillary Channel Structures, Improved Process For Making Channel Structures And Extrusion Die For Use Therein," incorporated herein by reference. The capillary channel structures described in Thompson are collapse-resistant, and the capillary channel of the structures of Thompson are open along a substantial length in the axial direction of the structure such that fluid can be received from outside of the channel as a result of such open construction. These fibers can be heated gently to cause the fibers to curl. The curled fibers can be stretched straight at room temperature. Upon heating to body temperature, the fibers resume the curled configuration. By using a bundle of the stretched fibers, the individual fibers of the bundle curl upon delivery due to body heat/hydration to form a fibrous filter mat that can entrap emboli within the fibrous network. The appropriate number of fibers for the bundle can be selected empirically to yield the desired packing density in the resulting mat and corresponding effective pore size.

One means of creating copolymers with desired properties is to form a graft copolymer. A graft copolymer is prepared by linking together two different polymers, for example, by way of chemical initiation (10) or radiation (11) in the form of ultra violet light, gamma or x-ray irradiation. A graft copolymer can exhibit properties closely related to the two parent compounds. Some copolymer embodiments harbor the tensile strength and biostability of polyethylene terephthalate and the super absorbent swelling of polyacrylamide.

Polyethylene terephthalate (PET) polyester has been used extensively in medical devices including sutures and large diameter vascular grafts with good clinical success. (12) The molecular formula for PET is H—[O—$(CH_2)_2$—O—CO—$(C_6H_4)$—CO]$_n$—R where R can be, for example, OH (Dacron®) or $OCH_3$ (terylene), and the chemistry and fiber manufacture is well worked out. The FDA has approved PET for such implants as fabric used in suture (temporary implant) or sewing rings for heart valves (permanent implant). (13) Given these characteristics, PET is suitable as the base material for an embolism protection device.

Polyacrylamide belongs to the class of hydrogels known as super absorbent polymers. These polymers swell in the presence of aqueous solutions and can increase to 1000 times their original size. (14) The ability of polyacrylamide to swell can contribute significantly to the efficacy of some embodiments of the device design proposed here. However, placing such a material in the vasculature involves appropriate control of swelling parameters to avoid vessel harm from excessive swelling. In addition, swelling can cause changes in polymer porosity. (30) A pore size that is too small may hinder blood cell flow, while a pore size that is too large may allow emboli to pass. The design of the device contributes significantly to porosity, however porosity associated with swelling can also contribute to the function of entrapping emboli.

The desirability of polyacrylamide as a material for the devices described herein stems at least in part from its chemical structure. Polyacrylamide is derived from acrylamide monomer units. The molecular formula is —[CH$_2$CHCONH$_2$—]$_n$—. Polyacrylamide is a linear hydrogel which can react with many kinds of compounds to produce derivatives of polyacrylamide with many valuable properties such as flocculation, thickening and surface activity. (16, 29) This reactivity allows for addition of functional groups, which may alter its physical properties. In addition, there is a group of special polyacrylamide copolymers called super absorbent polymers. (17, 21) These polymer can absorb water ten to one-thousand fold of their original weight and, under certain pressure, do not dehydrate. During expansion, super absorbent polymers are capable of delivering agents to the surrounding microenvironment, which is a quality useful for delivery of thrombolytic agents from corresponding devices. Super absorbent hydrogels are also further described in U.S. Pat. No. 6,271,278 to Kinam et al., entitled "Hydrogel Composites And Super Porous Hydrogel Composites Having Fast Swelling, High Mechanical Strength, And Superabsorbent Properties," incorporated herein by reference. As with PET polyester, polyacrylamide is approved by the FDA for use in medical adhesives. (18) The FDA approval of the material together with its material properties makes polyacrylamide a suitable polymer and/or copolymer for use in the embolism protection devices described herein. Polyacrylamide has been used as a controlled release vehicle for antimicrobial agents. (28)

Extensive studies have been conducted on the swelling and deswelling of polyacrylamide. (26) Several factors contribute to the swelling properties of polyacrylamide including swelling agent composition, curing time, degree of hydrolysis, temperature and cross-linking. Cross-linking is most intimately tied to swelling, for swelling is described as the process necessary to attain equilibrium between thermodynamic expansion (Flory-Huggins theory, 1953) and the retractive force of the cross-linked structure. There are several means to alter cross-link degree and formation including alteration of preparation physical state (dry vs. wet), cross-linking duration, and cross-linking agent. A recent study investigated the effect of several different cross-linking agents on polyacrylamide gel swelling. (27) In brief, a 5×5 cm piece of polyacrylamide gel was dehydrated and weighed. The sample was then immersed in 100 ml of distilled water, and the weight of the samples was taken at 10 minute intervals. The weight degree of swelling, q, (ratio of the weight of the swollen sample to that of the dry sample) was plotted as a function of time. Results indicate a greater than six-fold change in weight degree of swelling simply by altering the cross-linking agent. Control of polyacrylamide hydrogel porosity and crosslinked density is described further in U.S. Pat. No. 6,391,937 to Beuhler et al., entitled "Polyacrylamide Hydrogels And Hydrogel Arrays Made From Polyacrylamide Reactive Prepolymers," incorporated herein by reference. By varying the crosslinking agent, prepolymer properties and the degree of crosslinking, the porosity of the hydrogel can be controlled to satisfy desired device parameters.

In some embodiments, block copolymers can be used to introduce a stable form of a polymer blend in which the hydrogel is bonded to a structural polymer. In particular, the hydrogel can be grafted onto the structural polymer material based on knowledge in the art. In particular, polymeric materials have been grafted together using plasma, although other crosslinking approaches can similarly be used. A high-energy plasma technique generates active groups in the polymer, which facilitate the grafting of the second substrate to the first. The chemical composition of the two materials are complementary to this potential bonding and have been individually used to generate graft copolymers. (24) This copolymer matrix has the potential to swell and develop significant porosity in a controllable fashion. This reaction results in the grafting of polyacrylamide onto the (PET) fibers. This grafting can be further or alternatively facilitated with ultraviolet crosslinking. (25) (See Equation 1.)

Reaction of Polyacrylamide and PET Polyester

—[O—(CH$_2$)$_2$—O—CO—C$_6$H$_4$—CO]$_n$   +   (plasma)   +

—[CH$_2$CHCONH$_2$]$_n$—   $\longrightarrow$   media (PET:PAM)

(1)

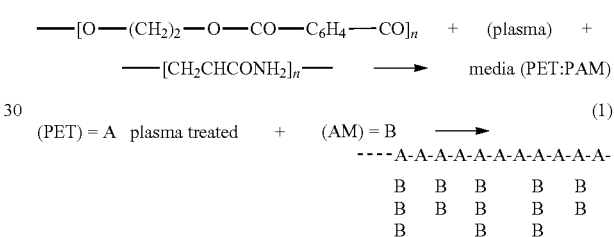

In some embodiments, the embolism protection device comprises a biodegradable/bioresorbable polymers. These embodiments may or may not further comprise a biologically active agent that is released by the degradation of the biodegradable polymer following implantation within a patient. Suitable biodegradable polymers include, for example, polysaccharides, such as polydextran, cellulose and starch, hydroxyethyl starch, derivatives of gelatin, polyvinylpyrrolidone, polyvinyl alcohol, poly[N-(2-hydroxypropyl)methacrylamide], poly(hydroxyacids), poly(epsilon-caprolactone), polylactic acid, polyglycolic acid, poly(dimethyl glycolic acid), poly(hydroxybutyrate), copolymers thereof and mixtures thereof.

To form the desired structures from the polymers, the polymers during the crosslinking/grafting step can be molded into the desired form. Various molding techniques can be used, such as injection molding, casting, compression molding and the like. However, other polymer processing approaches can similarly be used, such as extrusion, calendering, blowing and the like. In particular, foam materials can be formed conveniently by extrusion, and composite materials can be formed by coextrusion. In some embodiments, the porosity is introduced through a particulate pore forming agent that is combined with the polymer during processing and subsequently removed, such as by dissolving the particles while leaving the polymer intact, to leave the pores. The nature of the porosity is determines in part from the nature of the pore forming materials. If sponge-like materials are formed by foaming, non-uniform pressure can be applied to the expanding foam to change the resultant porosity.

Additional materials, such as metals, can be introduced into the polymer to render the device radio-opaque such that it can be visualized via angiography or clinical techniques. Biocompatible metals include, for example, titanium, titanium-nickel alloys, and stainless steel. Guidewires, tethers and the like can also be formed from these biocompatible metals and/or biocompatible fibers, which can be formed from the same materials as the biocompatible fabrics described below. Also, the embolism protection device can further comprise a biocompatible adhesive, especially on the exterior of the device to facilitate anchoring of the device at the place of delivery. Suitable biocompatible adhesives include, for example, commercially available surgical adhesives, such as cyanoacralate (such as 2-octyl cyanoacrylate from Ethicon Products), fibrin glue (such as Tissucol® from Baxter) and mixtures thereof.

Also, the exterior can be covered with a biocompatible fabric. Biocompatible fabrics can be formed from a variety of materials, such as silk, nylon and/or polyesters, including, for example, Dacron® polyester. The fabric can be selected to have a porosity smaller than the porosity of at least a portion of the remaining device or no porosity, such that trapped emboli generally do not pass through the fabric upon the removal of the device from the patient. Similarly, the embolism protection device can have a coating, such as a polymer coating, which can be formed by stray coating or dip coating a polymer solution or a polymer melt, which forms the polymer coating upon drying or cooling, respectively. Such a polymer coating may not be inherently porous, and desired porosity can be introduced by mechanically puncturing the coating with a fine needle or the like or by laser drilling appropriate pores. A wide variety of lasers with moderate power can be used for the drilling and conventional optics can be used to focus the laser beam to produce the desired pore size.

Bioactive Agents

The embolism protection devices alone provide control over the movements of emboli within the patient's vessel. However, it may be desirable to combine the mechanical features of the device with biologically active agents to provide another dimension to the treatment. The association of bioactive agents with the device can both provide treatment to shrink or eliminate emboli within the device and/or also to deliver a bioactive agent downstream from the device. Suitable bioactive agents include, for example, thrombolytic (anti-thrombogenic) agents, anti-platelet agents, anti-coagulation agents, growth factors and combinations thereof.

Suitable thrombolytic agents include, for example, tissue-type plasminogen activator (tPA), mutated forms of tPA, such as TNK-tPA and YM866, urokinase, streptokinase, staphylokinase, and the like. In particular, tPA is a polypeptide that acts upon plasminogen to form plasmin. Plasmin breaks down fibrin, one of the main structural proteins in blood clots. (22, 23) Plasmin also lyses fibrinogen, a precursor of fibrin. tPA can be produced according to the method described in U.S. Pat. No. 4,935,368 to Ryotaro et al., entitled "Process For Producing Tissue Plasminogen Activator," incorporated herein by reference. An effective precursor of tPA is described in U.S. Pat. No. 6,001,355 to Dowdle, entitled "Pro-tPA For The Treatment Of Thrombosis, Embolism And Related Conditions," incorporated herein by reference. Analogs, i.e. mutated forms, of tPA are known, for example, as are described in U.S. Pat. No. 5,106,741 to Marotti et al., entitled "Tissue Plasminogen Activator (TPA) Analogs," published PCT application WO 93/20194 to Sato et al., entitled "TPA Analog," and PCT published application WO 02/22832 to Xia et al., entitled "A Cell Line Expressing Mutated Human Tissue-Type Plasminogen Activator, The Constructing Strategy Thereof And Methods Of Preparing Expressed Protein," all three of which are incorporated herein by reference. Elsewhere in this application including the claims, tPA refers to natural tPA, fragments thereof and analogs thereof that are effective to stimulate the formation of plasmin.

Together with a sound materials design, an embolism protection device associated with tPA can be capable of destroying emboli associated with cardiopulmonary bypass. Recent reports suggest that most of the emboli generated during cardiopulmonary bypass have a significant fibrin component. (19, 20) The body's primary means of degrading fibrin is via tissue plasminogen activator (tPA). tPA is currently in clinical use as a remedy for heart attack and stroke (thrombolysis, reperfusion therapy). This therapy involves delivering tPA through an intravenous line to break up and dissolve a clots in the coronary artery, thereby restoring blood flow. (21) tPA is of particular interest for use with embolism protection devices described herein given its high specificity for clot degradation without causing systemic bleeding events.

Suitable anti-platelet agents include, for example, acetylsalicylic acid, ADP inhibitors, phosphodiesterase III inhibitors, glycoprotein IIB/IIIA inhibitors, adenosine reuptake inhibitors, nitrates, such as nitroglicerin and isosorbide dinitrate, and Vitamin E. Suitable anti-coagulation agents include, for example, heparin, warfarin, and the like. Suitable growth factors include, for example, vascular endothelial growth factor (VEGF) and the like.

In some embodiments, materials are incorporated into the device that form by decomposition a therapeutic composition. For example, nitric oxide (NO) can stimulate beneficial vascular responses. Compounds with an $NONO^-$ functional group can emit nitric oxide following implantation of the medical device. Suitable compositions include, for example, $(CH_3)_2CHNHNONO^-$, $(CH_3CH_2)_2NNONO^-$, $H_2N(CH_2)_3NHNONO^-$, $NaNONONa$. The synthesis of 1-(2S-carboxy-pyrrolidin-1-yl)-oxo-2-hydroxydiazene disodium salt, 1-hydroxy-2-oxo-3-carboxymethyl-3-methyl-1-triazine N-methylamide disodium salt, 1-hydroxy-2-oxo-3-carboxymethyl-3-methyl-1-triazine N-methylamide sodium salt, the bis(nitric oxide) adduct of L-prolyl-L-leucylglycinamide, and corresponding protein adducts are described in U.S. Pat. No. 5,632,981 to Saavedra et al., entitled "Biopolymer-Bound Nitric Oxide Releasing Compositions, Pharmaceutical Compositions Incorporating Same And Methods Of Treating Biological Disorders Using Same," incorporated herein by reference. Conjugates of heparain, for example with dermatan sulfate, that are effective to prevent thrombosis are described in U.S. Pat. No. 6,491,965 to Berry et al., entitled "Medical Device Comprising Glucosaminoglycan-Antithrombin III/Heparin Cofactor II Conjugates," incorporated herein by reference. Furthermore, some polymers decompose to form an acidic moiety, such as polyhydroxybutyrate degrading to 3-hydroxyvaleric acid.

The bioactive agent can be associated with the materials of the embolism protection device by one or more approaches. For example, the device can be contacted with a solution of the agent such that the agent can be infused within the device. The agent is then released, possibly gradually, upon implantation of the device. For example, during expansion, super absorbent polymers can be capable of delivering agents to the surrounding microenvironment, a quality appropriate for delivery of thrombolytic agents or other bioactive agents. In other embodiments, the bioactive agents are placed in contact with the polymers during the polymerization and/or crosslinking/grafting steps such that the bioactive agents are incorporated within the polymer matrix. The bioactive agents then elute following implantation.

For systemic administration, the therapeutic dose of tPA for a human patient can be 0.01 to 80 micro moles (70-8750 ng/ml) but is thought to be most effective at 500-1000 ng/ml. (31) Lower doses may be effective with local delivery since the local concentration can be higher over the delivery period. An appropriate corresponding dose for local delivery can be sustained throughout the time of implant. If the dose is released too quickly, a toxic environment can ensue (>25,000 ng/ml for systemic delivery). (32) To determine the initial loading dose, the release kinetics of tPA from the device can be used to deliver a desired dose of tPA or other biologically active agent. An empirical evaluation of an appropriate dose can be estimated from in vitro studies, such as the flow loop studies described below, or in animal studies. In some embodiments, it may be desirable to deliver the biologically active agent with a suitable biocompatible carrier. Suitable biocompatible carriers can be, for example, a physiologically buffered saline. Suitable buffers can be based on, for example, the following compounds: phosphate, borate, bicarbonate, carbonate, cacodylate, citrate, and other organic buffers such as tris(hydroxymethyl)aminomethane (TRIS), N-(2-hydroxyethyl) piperazine-N'-(2-ethanesulfonic acid) (HEPES) or morpholine propanesulphonic acid (MOPS). The ionic strength of the biocompatible carrier can be adjusted by the addition of one or more inert salts including, for example, NaCl, KCl and combinations thereof. Preferably, the ionic strength is near physiological values.

Additionally or alternatively, genes coding for desired polypeptide-bioactive agents can be delivered in a vector. The vector can be taken up by adjacent cells and expressed as the protein. Suitable vectors are known in the art, and include, for example, viral vectors, plasmids and the like. In particular, a vector encoding tPA can be delivered through the device. The effectiveness of a vector for tPA expression in rabbits is described further in Waugh et al., "Gene therapy to promote thromboresistance: Local over-expression of tissue plasminogen activator to prevent arterial thrombosis in an in vivo rabbit model, Proceeding of the National Academy of Sciences—USA 96(3): 1065-1070 (Feb. 2, 1999), incorporated herein by reference. Vectors, for example, plasmids and viral vectors, suitable for transforming human cells with appropriate control sequences for expression in human cells are described further in U.S. Pat. No. 5,106,741 to Marotti et al., entitled "Tissue Plasminogen Activator (TPA) Analogs," and U.S. Pat. No. 4,935,368 to Ryotaro et al., entitled "Process For Producing Tissue Plasminogen Activator," both of which are incorporated herein by reference.

Use Of the Embolism Protection Device

Nearly all cardiac surgical procedures and well as certain non-cardiac procedures and natural events, such as kidney stone formation, result in the generation of emboli, in the broad sense used herein. Emboli generation frequently causes life altering, and possibly life threatening neurological disturbances. The emboli protection device described herein can be useful for all patients undergoing cardiac surgery and for other procedures. In some embodiments, the elegant design employs a unique combination of FDA approved materials and therapeutic agents to provide an easy to use and effective means of controlling embolic events. At some point following the delivery of an embolism protection device, it may be desirable to remove the device or a portion thereof.

In general, embolism protection devices can be supplied to medical professionals in a range of sizes, such that an appropriate size can be selected from the available sizes for a particular patient and for a particular point of placement. Due to the expanding nature of the embolism protection device a precise size device is not required since the device conforms over a reasonable range to the vessel. Nevertheless, imaging techniques and estimates from experience and the patient's size can provide an appropriate estimate for the appropriate size of the embolism protection device. An embolism protection device can be placed within the desired vessel of a patient with a catheter, a syringe, a guidewire or the like. In particular, an embolism protection device can be attached to a guidewire to feed the device through a catheter to a desired position in a vessel within a patient. The guidewire can be separate from the device following the placement of the device, or the guidewire can remain tethered to the device to facilitate maintaining the device at the desired position and/or to facilitate removal of the device. Removal of the guidewire can be performed by pulling out the guidewire if the guidewire is not attached to the device and if the device is applying sufficient force against the walls of the vessel such that friction can hold the device in place. If the guidewire is to remain attached to the device, the guidewire can be attached to the device with a mechanical attachment or with an adhesive. The guidewire can be mechanically attached to the device, for example, by forming the polymer around the end of the wire, generally with a non-straight section of wire, winding the wire around a section of the device and/or heat strinking a portion of the polymer around the end of the wire.

Figure 12:
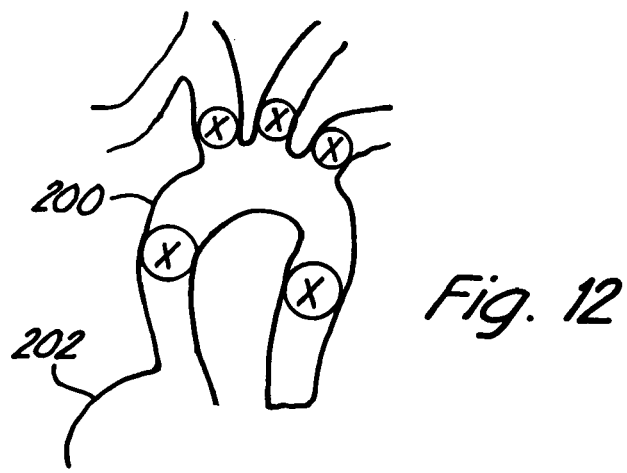
FIG. 12 is a schematic view showing possible positioning of embolism protection devices within an aorta and corresponding branch vessels.

Due to the potentially serious outcomes of cardiac intervention that can result in emboli associated with the aorta, the embolism protection device can be positioned at one or more positions within the aorta or in arteries branching from the aorta. Referring to FIG. 12, aorta 200 is shown adjacent heart 202. As shown in FIG. 12, five embolism protection devices 204, 206, 208, 210, 212 are shown in different positions. Any one or more of these can be used for a particular patient. Devices 204-212 are shown with device 204 in the ascending aorta, device 206 in the descending aorta, device 208 in the innominate artery, device 210 in the left common carotenoid artery and device 212 in the left subclavian artery.

Figure 13:
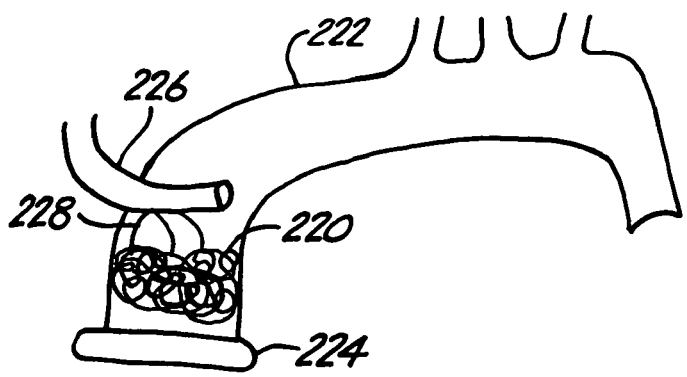
FIG. 13 is a schematic view of an embolism protection device associated with an aortic cannula during cross-clamp bypass.
Figure 14:
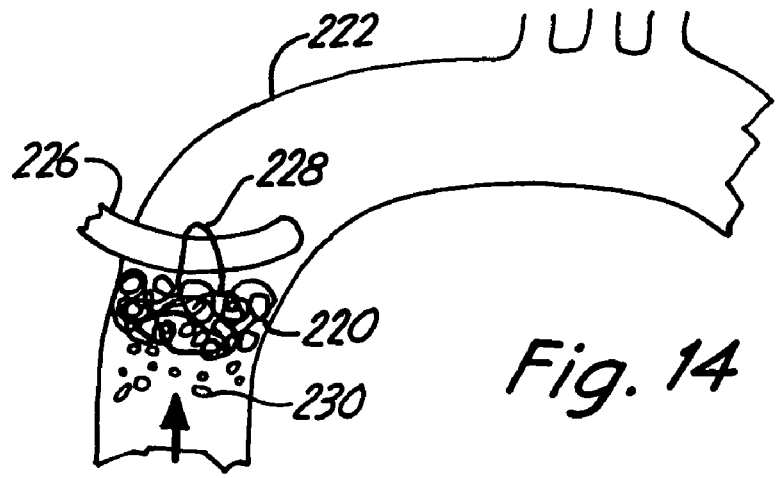
FIG. 14 is a schematic view of the embolism protection device of FIG. 13 following removal of the cross-clamp.

Referring to FIG. 13, an embodiment is shown that is appropriate for use when the heart is on bypass. In particular, this device can be placed in the aorta distal to the site of cross clamp in a cardiac surgical procedure involving cardiopulmonary bypass. In this embodiment, an embolism protection device 220 is within the ascending aorta 222 distal to cross clamp 224 and is attached to an aortic cannula 226, for example, with a fastener 228, such as a loop of material, a clip, anchor, a catching device or the like. An aortic cannula generally can be used to return blood to the heart when the heart is on bypass. For example, the heart can be placed on bypass during a procedure to repair portions of the heart. Aortic cannula are known in the art, and one embodiment is described in U.S. Pat. No. 6,387,087 to Grooters, entitled "Aortic Cannula," incorporated herein by reference. Attachment to aortic cannula 226 stabilizes device 220 at the pressures experienced during the cross clamp procedure. Referring to FIG. 14, release of cross clamp 224 can result in the corresponding release of emboli 230 that are trapped by embolism protection device 220. Device 220 can release bioactive agents to dissolve emboli 230, and, additionally or alternatively, removal of device 220 can remove trapped emboli. For example, device 220 can be removed from the cannula site shortly following the removal of the cannula.

Figure 15:
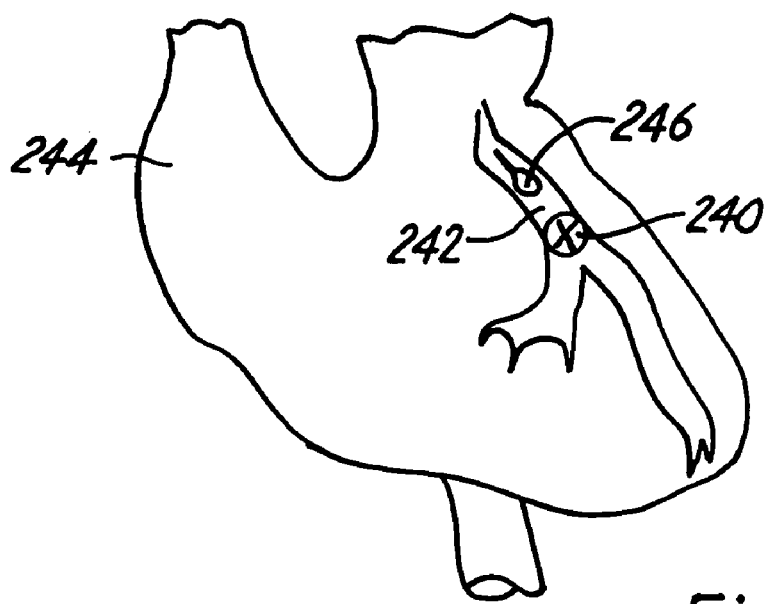
FIG. 15 is a schematic view of an embolism protection device deployed in a coronary artery.

In some embodiments, an embolism protection device can be placed within a coronary artery. In particular, the embolism protection device can be placed down stream from a planned site of intervention, for example, by angioplasty, placement of a bypass graft or introduction of a stent. Referring to FIG. 15, embolism protection device 240 is shown within coronary artery 242 of heart 244. Device 240 is located downstream in the artery from an intervention site 246.

Figure 16:
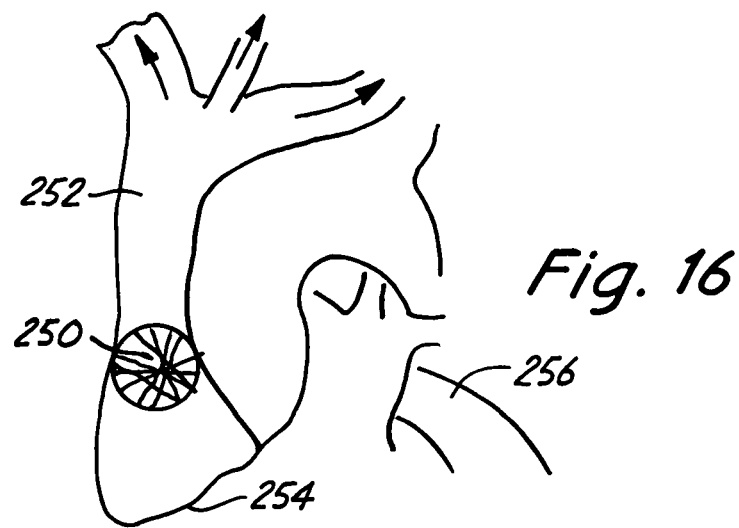
FIG. 16 is a schematic view of an embolism protection device in the pulmonary artery.
Figure 17:
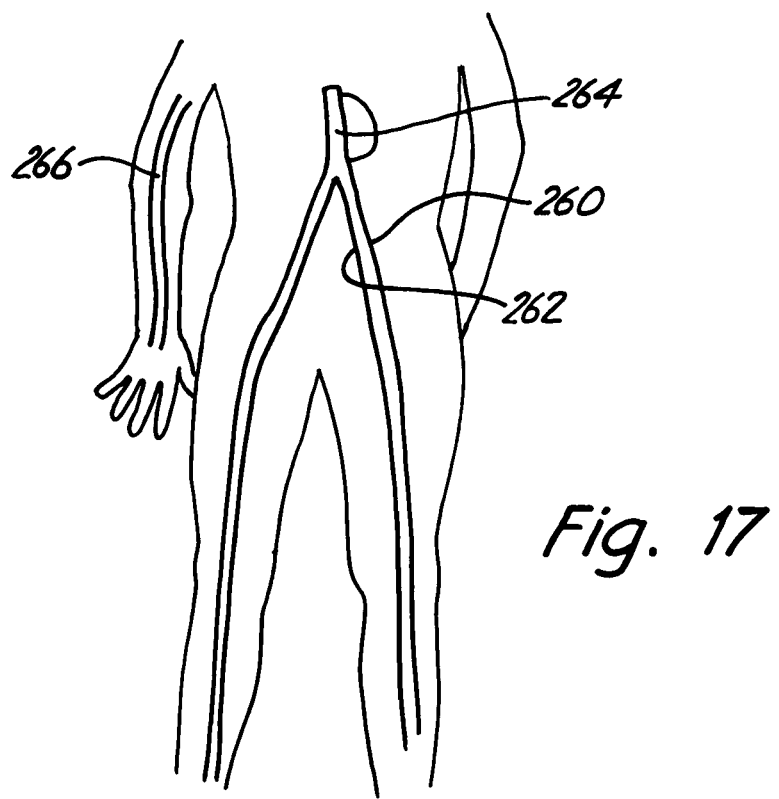
FIG. 17 is a schematic view of an embolism protection devices positioned in blood vessels in a patient's leg and arm.

In other embodiments, an embolism protection device can be place in the venous side of the heart/vascular system to prevent emboli to the lungs. Referring to FIG. 16, embolism protection device 250 is within the pulmonary artery 252 downstream from the pulmonary heart valve 254 where pulmonary artery 252 attached to heart 256. Flow from the pulmonary artery goes to the lungs. More generally, an embolism protection device can be placed within any vessel in the body. As shown in FIG. 17, devices 260, 262 are within arteries leading to the leg from the descending abdominal aorta 264 while device 266 is in an arm. Embolism protection devices can be similarly placed in veins.

Figure 18A:
FIG. 18A is (left) a schematic side view of a two-component embolism protection device downstream from a plaque deposit and (right) an enlarged cross sectional view of an embodiment of a surface capillary fiber.
Figure 18B:
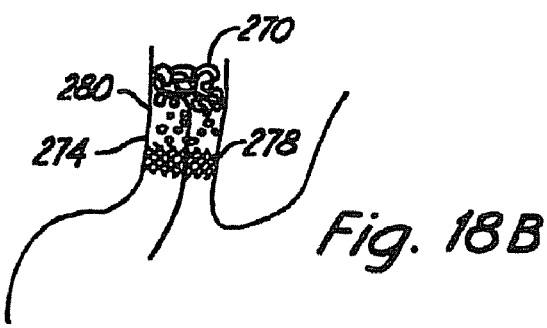
FIG. 18B is a schematic view of the device of FIG. 18A following deployment of a stent at the plaque deposit.
Figure 18C:
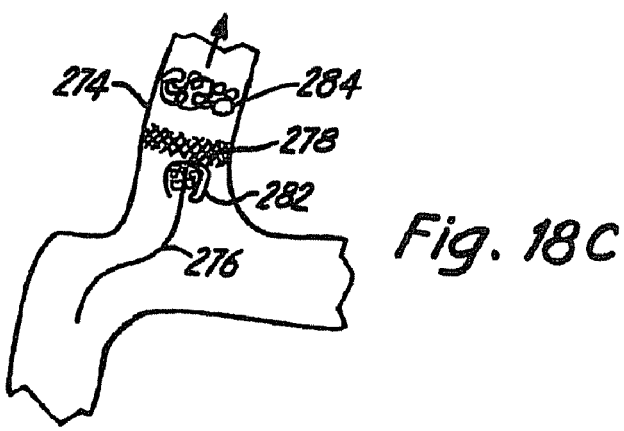
FIG. 18C is a schematic view of the removal of one component of the embolism protection device of FIG. 18A.

As noted above with respect to FIG. 12, the embolism protection device can comprise two distinct portions or similarly can be used with a separate but associated drug delivery article. Use of such devices in the context of the application of a stent is shown in FIGS. 18A, 18B and 18C. As shown in FIG. 18A (left), a two component embolism protection device 270 is placed downstream from a plaque deposit 272 in vessel 274. In this embodiment, device 270 comprises a tether 276 to facilitate removal, although other removal approaches can be used. FIG. 18A (right) is a schematic enlarged view of a cross section of a surface capillary fiber showing one or more grooves 271 on the surface of the fiber of the embolism protection device 270. As shown in FIG. 18B, a stent 278 has been applied to plaque deposit 272 with the potential generation of emboli 280, which are trapped by embolism protection device 270. As shown in FIG. 18C, an embolism trapping portion 282 of device 270 is being removed using tether 276, while a bioactive agent eluting portion 284 of device 270 remains in vessel 274.

Figure 19:
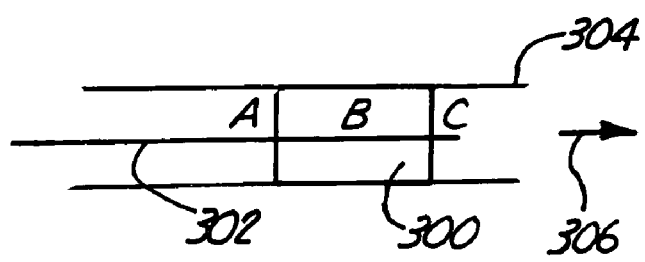
FIG. 19 is a side view of an embolism protection device associated with a guide-wire through which a biologically active agent is delivered at one or more of locations A, B and C.

The elution of a bioactive agent from the embolism protection device is described above. Additionally or alternatively, one or more bioactive agents can be delivered through a guidewire or the like tethered to the embolism protection device. The guidewire can have a small inner channel that has an opening into the vessel at or near the proximal end. The flow rate and time determines the dose of biologically active agent delivered into the vessel. Referring to FIG. 19, embolism protection device 300 associated with guidewire 302 is within a body vessel 304. Guidewire 302 has a small internal channel that can have an opening at point A, B and/or C. The natural flow direction in the vessel is indicated by arrow 306. Delivery of a biologically active agent at point A results in the flow of the agent through device 300 and downstream. Delivery of the agent at point B results in a concentration of the agent within the device with any residual agent flowing downstream. In addition, delivery of the agent at point C results in delivery of the agent downstream from the device.

Once the embolism protection device has served its purpose, it may be desirable to remove the device or a portion thereof. For example, shortly after completing a procedure, the device may have had the opportunity to collect and/or dissolve the emboli of significance. Alternatively, once the embolism protection device has completed eluting a biologically active agent following the trapping and/or dissolving of emboli associated with a procedure or other event, it may be desirable to remove the device. Removal of the device can take place, for example, minutes, hours, days, months or years following delivery depending on the particular device and its intended purpose.

As noted above, in some embodiments, an embolism protection device can be attached to one or more tethers or the like such that pulling on the tethers tends to reduce the size of the device such that it can be moved upstream from its delivered position. In other embodiments, an embolism protection device can have a reduced diameter or pointed tip at the proximal end. With a reduced diameter proximal end and a compressible polymer structure generally possessed by the device, the device can be pulled within a sheath using a tether due to the forces applied to the device at the end of the sheath. Once the device is confined within the sheath, the device can be withdrawn from the vessel with the sheath.

In alternative or additional embodiments, an extraction device can be used to facilitate removal of the embolism protection device. An extraction device comprises a gripper that can grip the embolism protection device and reduce the diameter of at least a portion thereof. The gripper can be positioned within the vessel through a catheter or the like. An actuating wire or other control device can connect the gripper with a control handle at the proximal end of the gripper device outside of the patient. Thus, the gripper can be manipulated by a health care professional from outside of the patient using appropriate visualization techniques, such as a fiber optic based visualization systems for minimally invasive surgical procedures.

Figure 20:
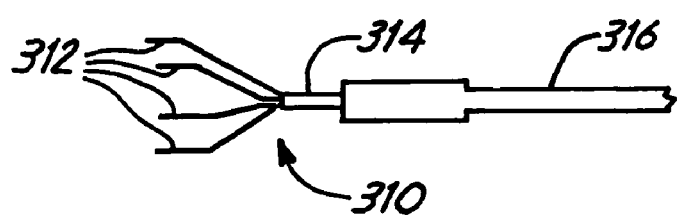
FIG. 20 is a side view of a gripper device to facilitate removal of an embolism protection device.

An embodiment of a suitable gripper is shown in FIG. 20. Gripper 310 has a gripping portion with four flexible arms 312 extending from a shaft 314. Shaft 314 can have a hollow core for threading the shaft over a guide-wire or the like. An outer shaft 316 can move in position relative to shaft 314. Outer shaft 316 can engage arms 312 and deflect them toward the center of shaft 314. This deflection of arms 312 results in a gripping function. Thus, if arms 312 are positioned along the outer surface of an embolism protection device, the deflection of arms 312 toward a center axis compresses the embolism protection device correspondingly. This deflection can be continued until the gripper and the embolism protection device has a small enough profile for removal from the vessel. For embodiments of an embolism protection device with a plurality of sections, gripper 310 can be used to facilitate removal of a portion of the embolism protection device oriented toward the gripper. Furthermore, various other gripper configurations, including, for example, some configurations developed for use with catheters for other functions can be adapted for use in removing an embolism protection device.

EXAMPLES

Example 1

Synthesis of Hydrogel Grafted Polymer

This example demonstrates the synthesis of a polyacrylamide hydrogel polymer grafted onto a PET polyester polymer.

Medical grade PET fibers were surface activated by subjecting them to an oxygen plasma. The plasma glow discharge system primarily consisted of a barrel radio frequency (RF) plasma reactor with a diameter and depth of six inches (Extended Plasma Cleaner, Harrick Scientific, Ossining, N.Y.). The pressure was monitored by a thermocouple vacuum gauge (Hastings Vacuum Gauge, DV-6). The reaction chamber was evacuated to 10 millitorr (mtorr) to remove contaminants and moisture. The chamber was then flooded with research grade oxygen gas (99.99%), and evacuated until a constant pressure of 150 mtorr was established, at which point RF plasma of 30 Watt was applied for ten minutes. Activated fibers were then dip coated with a mixture of polyacrylamide (10% by weight (wt)), acrylamide monomer (10%-20% by wt), and methylenebis-acrylamide (0.05-0.1% by wt crosslinker) and a UV sensitive initiator in water. The grafting was allowed to cure under a UV lamp for 10 minutes.

Figure 21:
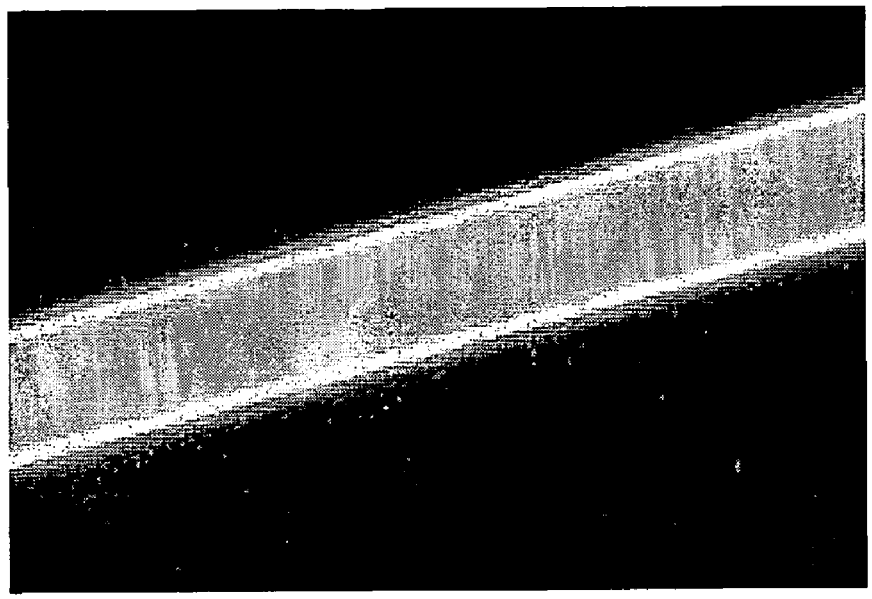
FIG. 21 is a photomicrographs of a PET fiber.
Figure 22:
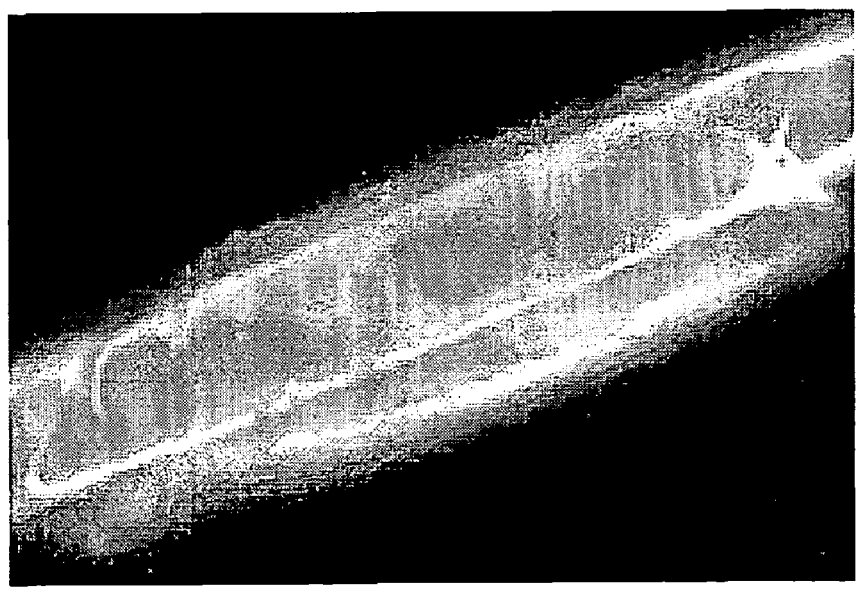
FIG. 22 is a photomicrograph of a PET fiber with grafted with a polyacrylamide hydrogel.

Visual inspection and microscopic techniques verified matrix synthesis. See FIGS. 21 and 22. The grafted copolymer matrix was then characterized using swelling control studies.

Example 2

Incorporation of Biological Agent into Hydrogel and Controlled Release

This example demonstrates the incorporation of tPA into a polyacrylamide (PAM) polymer and the subsequent release of the tPA.

In this experiment, tPA was incorporated into a polyacrylamide hydrogel by dispersion into the polymerization solution at the time of polymerization. This method may result in the entrapment of the tPA in the interstices of the gel-like matrix where it is held until hydration at which time the agent is slowly released.

A 2.8 ml solution was prepared comprising 1.5 ml-5 weight % acrylamide solution (approximate final concentration based on a volume per volume dilution 2.67% acrylamide), 6 µl-human two-chain tPA (2.2 mg/ml, from Molecular Sciences, MI), 9 µl-10% ammonium persulfate, 2.25 µl-TEMED (N,N,N',N'-tetramethylenediamine, 99% solution) and deionized water. The ammonium persulfate produces free radicals faster in the presence of TEMED such that the addition of TEMED to the mixture accelerates the polymerization and crosslinking of the gel. Three aliquots of 500 µl gels were made in glass test tubes and allowed to polymerize for 1 hr at room temperature (total tPA conc. 4.4 micromolar µM in each gel), thus creating three gels. Upon onset of polymerization, 50 µl of the control samples were removed and kept at −80° C.

The release kinetics of the tPA was analyzed. After polymerization, the gels were carefully removed from the test tubes and put in 20 ml vials. The test tube was rinsed with 5 ml of phosphate buffered saline (PBS), and the rinse poured over the gel in the 20 ml vial. This was slightly shaken to rinse the gel and to remove any unincorporated tPA. A 50 µl quantity of this solution was frozen. The remainder was poured off and replaced with another 5 ml of PBS. Both the gels and the controls were kept at 4° C. for the release experiment in an effort to prevent protein degradation and slightly shaken on an oscillating shaker. At designated time points, 50 microliter (µl) aliquots of buffer were taken. The amount of tPA in each aliquot was determined via ELISA (Diapharma Group, Inc. Westchester, Ohio). In brief, buffer samples were transferred in 100 µl volumes to wells of a 96-well plate containing anti-tPA IgG. The samples were incubated for 2 hours at room temperature. Bound tPA was detected with HRP (horseradish peroxidase)—labeled Fab fragments of anti-tPA IgG followed by a peroxidase substrate. Colorimetric staining was detected and actual quantity determined via comparison to the included standards (Biopool International, Cat#101-442).

Figure 23:
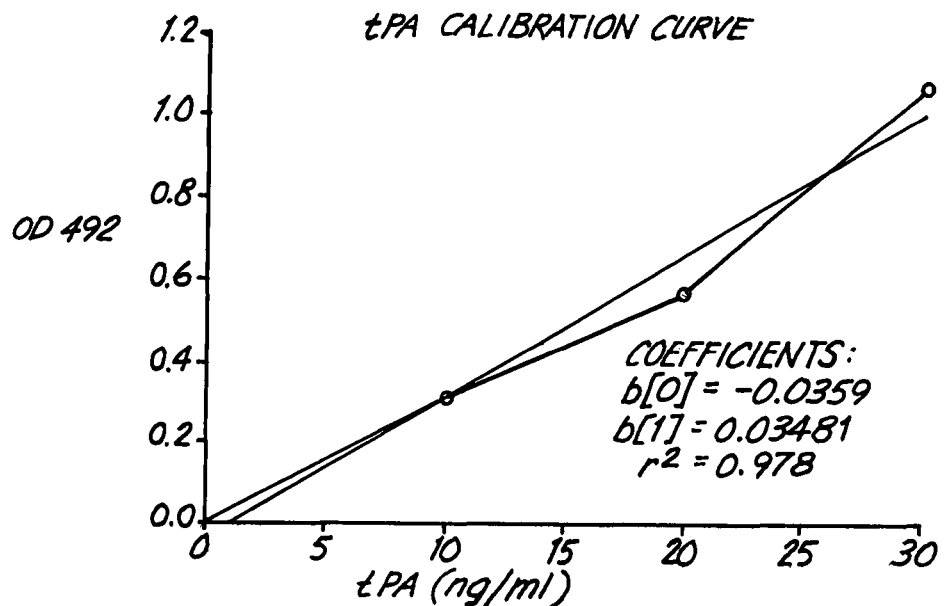
FIG. 23 is a plot of the standard curve for a tPA ELISA.

FIG. 23 shows the standard curve for the tPA ELISA. The curve was linear over the range tested with an R-squared value of 0.978. FIG. 23 is a plot of the experimentally measured time release kinetics of tPA from the hydrogel. Release of tPA from the hydrogel reached a maximum release of 31.4 ng/ml at 60 minutes.

We have demonstrated the ability to reliably produce a PET:PAM copolymer matrix. This matrix can be produced such that swelling is rapid, sustained and reproducible. In addition, tPA can be incorporated into the matrix. The release rate is typical of a hydrogel with an initial quick release sustained for at least 60 minutes following test initiation. This time duration would be sufficient for post-cardiopulmonary bypass cross-clamp embolism protection device filtration time, however further crosslinking alterations can be made to alter release. This release can be tailored after the toxic dose parameters and dose necessary for emboli destruction are determined.

Example 3

In Vitro Emboli Dissolution Test

This example demonstrates the effectiveness of recombinant human Tissue Plasminogin Activator (tPA) as a resolving agent with respect to the dissolution of porcine thrombolytic emboli in vitro.

tPA was diluted in phosphate buffered saline at the following concentrations: 1,000 nanograms/milliliter (ng/ml), 500 ng/ml, 100 ng/ml and 0 ng/ml. The emboli dissolution potential of each tPA solution was measured by applying the tPA solution to glass slides containing emboli and then measuring the change in emboli size as a function of time. To create the emboli, coagulated porcine whole blood was placed in a 5 cc syringe. Coagulated blood was extruded from the syringe and cut to uniform size (200-225 µm diameter); these uniform coagulated blood fragments will be referred to as "emboli". Emboli were placed on glass slides for microscopic measurement. Samples were labeled and measurement/descriptions were made for each embolus. Measurement was accomplished with a Zeiss® Microscope and Zeiss® LSM 4 software for image acquisition. One ml quantities of tPA solution were added to the characterized emboli and then placed on a shaker at 20 RPM in a testing room at 30-35° C.

Emboli size measurements were taken at various time points. Results are reported in Table 1 below.

TABLE 1

| tPA concentration | Sample # | Decrease in Geometric size | | |
|---|---|---|---|---|
| | | pre | Post | % change |
| 0 ng/ml | 1 | 233.0 | 231.0 | 0.86 |
| 0 ng/ml | 2 | 215.0 | 229.0 | 6.51 |
| 0 ng/ml | 3 | 216.0 | 223.0 | 3.24 |
| 0 ng/ml | average | 221.3 | 227.7 | 2.86 |
| 100 ng/ml | 11 | 222.0 | 216.0 | −2.70 |
| 100 ng/ml | 12 | 180.0 | 200.0 | 11.11 |
| 100 ng/ml | 13 | 176.0 | 173.0 | −1.70 |
| 100 ng/ml | average | 192.7 | 196.3 | 1.90 |
| 500 ng/ml | 51 | 221.0 | 201.0 | −9.05 |
| 500 ng/ml | 52 | 189.0 | 162.0 | −14.29 |
| 500 ng/ml | 53 | 221.0 | 190.0 | −14.03 |
| 500 ng/ml | average | 210.3 | 184.3 | −12.36 |
| 1000 ng/ml | 101 | 230.0 | 155.0 | −32.61 |
| 1000 ng/ml | 102 | 228.0 | 150.0 | −34.21 |
| 1000 ng/ml | 103 | 177.0 | 146.0 | −17.51 |
| 1000 ng/ml | average | 211.7 | 150.3 | −28.98 |

Thus, the tPA was effective at reducing thrombus size significant amounts.

Example 4

Evaluation with an In Vitro Flow Loop

This example demonstrates the utility of an in vitro flow loop for evaluation of an embolism protection device as well as provides an evaluation of two embodiments of an embolism protection device, one with tPA and one without tPA.

Figure 24:
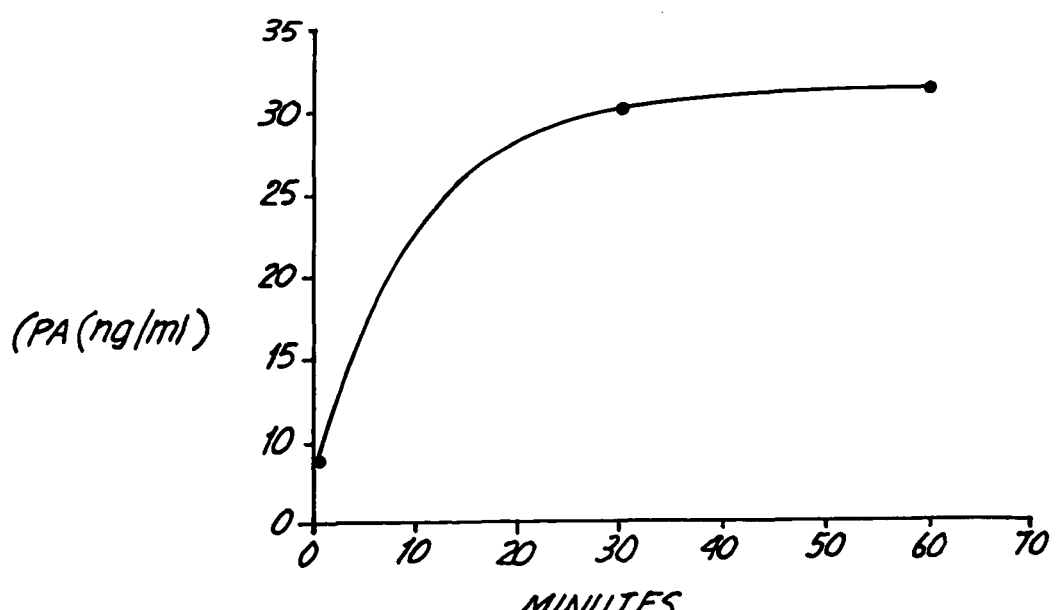
FIG. 24 is a plot of the elution of tPA from a hydrogel as a function of time, which provides information on the release kinetics.
Figure 25:
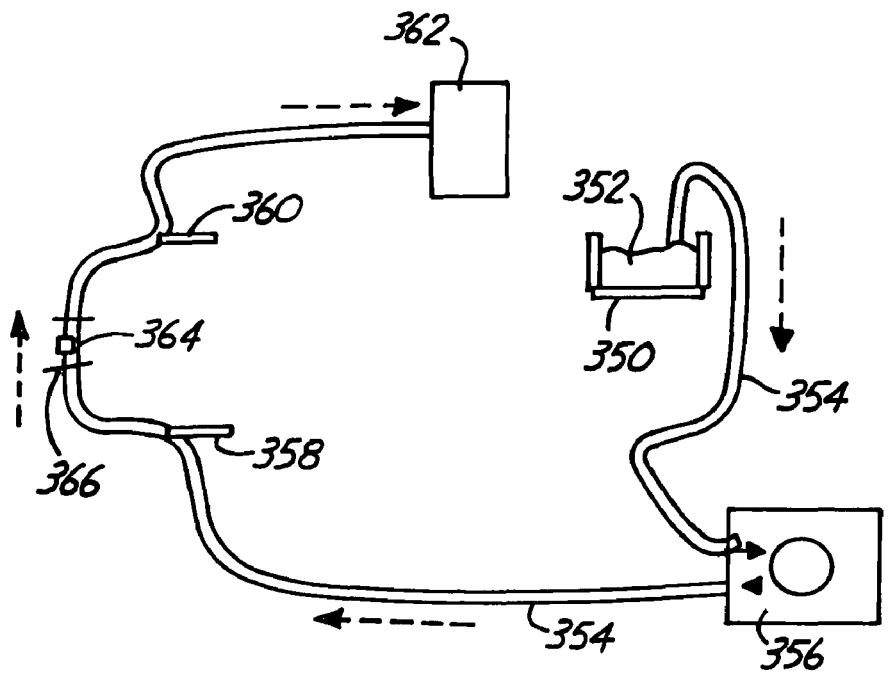
FIG. 25 is a diagram showing an in vitro flow loop.

The interrupted flow loop was developed to mimic the environment of a native coronary artery. The apparatus consisted of four components: a circulation unit, the embolism protection device, the blood/media, and the emboli. The flow loop was constructed as indicated in FIG. 24. The circulation unit had a heated reservoir 350 holding blood and media 352, tubing 354, a pump 356, injection ports 358, 360 and a collection vessel 362. Embolism protection device 364 was held in a fixture 366 within tubing 354. Flow through the system is noted in FIG. 24 with four flow arrows.

Figure 26:
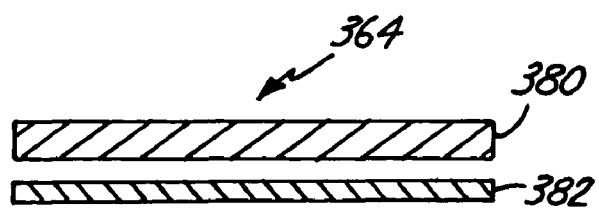
FIG. 26 is schematic side view of a composite embolism protection device with two materials prior to expansion.
Figure 27:
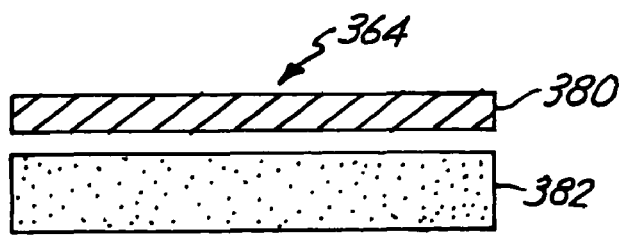
FIG. 27 is a schematic side view of the embolism protection device of FIG. 26 following expansion.
Figure 29C:
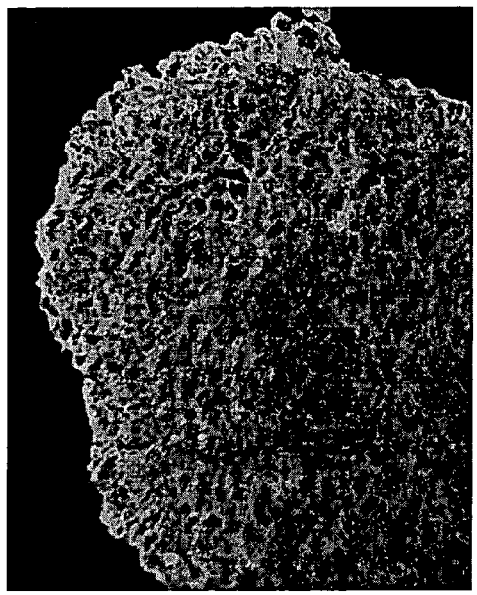
FIG. 29C is a micrograph of a fibrin emboli recovered from an embolism protection device that did not released tPA, at a magnification of 200×.
Figure 29D:
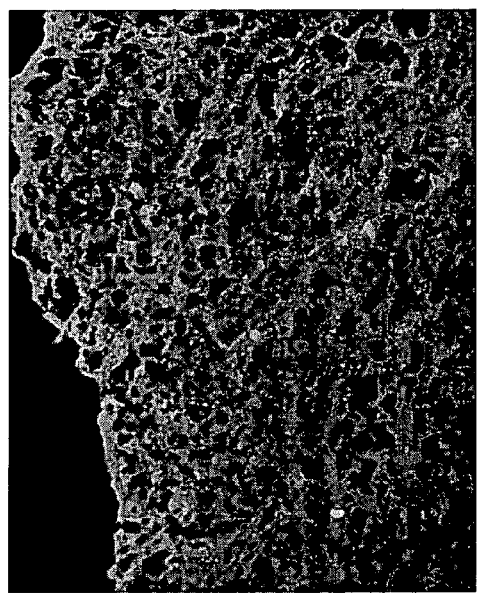
FIG. 29D is a micrograph of the fibrin emboli in FIG. 29C at a magnification of 400×.
Figure 29A:
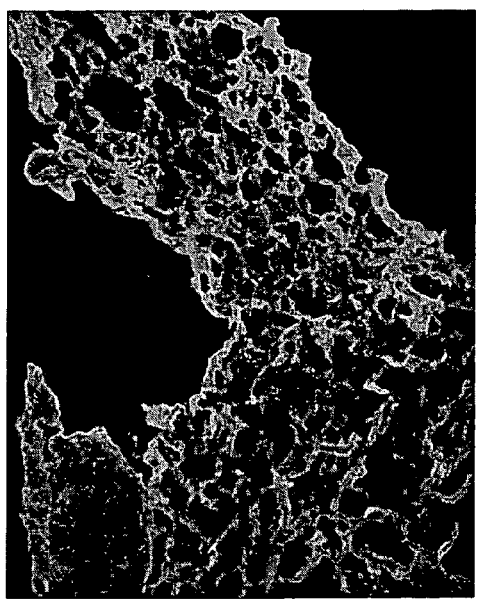
FIG. 29A is a micrograph of a fibrin emboli recovered from an embolism protection device that released tPA, at a magnification of 200×.
Figure 29B:
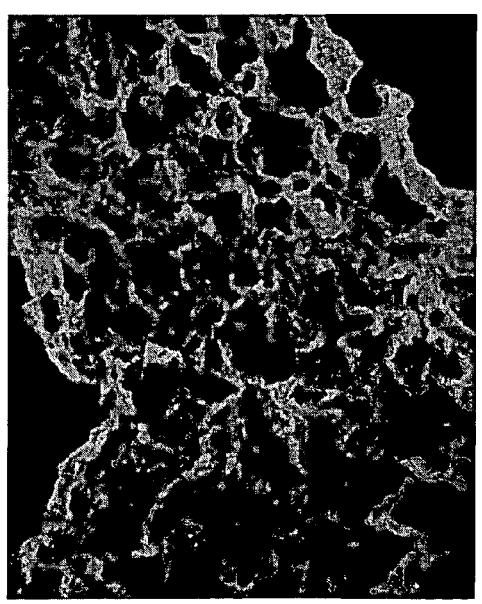
FIG. 29B is a micrograph of the fibrin emboli in FIG. 29A at a magnification of 400×.

Embolism protection device 364 was formed with two sections of structure. The layered system for purposes of this experiment was a polymeric construct that could both release tPA and trap the emboli based on an appropriate porosity. Referring to a schematic view of a pre-hydrated device 364 in FIG. 26, a first layer 380 was a nylon mesh polymer with a 70 micron pore diameter obtained from Sefar America Inc. Depew, N.Y. Layer 380 served to entrap emboli. A second layer 382 was a sponge-like layer made of polyacrylamide and impregnated with tPA. To incorporated tPA into layer 382, a solution was prepared comprising of 1.5 ml-5 weight % acrylamide solution (approximately 2.67% acrylamide final concentration based on a volume per volume dilution), 6 μl-human single-chain tPA (2.2 mg/ml, Molecular Sciences, MI), 9 μl-10% ammonium persulfate and 6.7 μl-TEMED. Three aliquots of 0.5 ml gels were made in glass test tubes and allowed to polymerize for 1 hr at room temperature, thus creating three gels. Following polymerization, each gel had a total TPA amount of 500 ng at a concentration of 1,000 ng/ml). The gels were removed from the tubes, and the nylon mesh layer was wrapped around the flat end and the sides of each gel leaving the rounded end of the gel from the bottom of the tube uncovered with the mesh. Each device when placed within the flow loop was positioned with the flat end downstream and with the round end upstream such that emboli are trapped by the mesh within the gel. Following contact with an aqueous solution, the gel expands to approximately twice its volume, as is schematically shown in FIG. 27, while the nylon mesh remains essentially unchanged, although it expands in response to the expansion of the gel. Due to the expansion of the gel, the pore size of the mesh may enlarge, but this enlargement was not directly measured.

Figure 28:
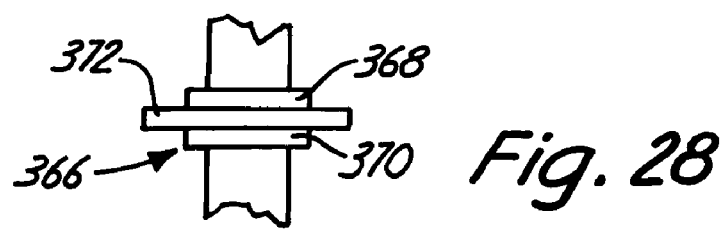
FIG. 28 is a side view of an embodiment of a mount for supporting an embolism protection device within the flow loop of FIG. 25.

Three two-layer embolism protection devices were constructed with tPA incorporation, and three two-layer devices were constructed without tPA incorporation using the solution described above except with no tPA. For these tests, a selected device 364 held by the test fixture 366. Referring to FIG. 28, test fixture 366 has two rings 368, 370 held together with a joining ring 372. Edges of device 364 are gripped between rings 368, 370 to fix device 364 in place.

Circulation of the media was performed with a centrifugal pump capable of generating flows from 30-120 ml/min. The tubing was a vinyl polymer with an inner diameter from 4-6 mm, similar to that of the native arterial vessels. The experiment was accomplished in a test chamber at 37° C. Injection port 358 upstream from the embolism protection device was used to introduce the test emboli. The medium flowing through the system was phosphate buffered saline. Emboli were generated by placing 1 ml of pig animal blood in a syringe and allowing it to clot (see above for determination of emboli size). The flow loop was validated using a calibrated flowmeter.

The emboli were introduced into the flow system at a concentration of approximately 15 emboli/ml of buffered saline. The time line for the testing was as follows:

0 time—introduction of device
1 sec.—Begin flow of media (buffered saline)
10 sec—Measure flow rate
15 sec—Inject emboli
30 sec—Collect aliquot #1 (of effluent, i.e. media past device.)
60 sec—Collect aliquot #2
100 sec—Collect aliquot #3
200 sec—Collect aliquot #4
300 sec—Collect aliquot #5

After about five minutes, the flow was stopped and the device removed and photographed microscopically. The device was then fixed for histological analysis. Aliquots of collected liquid were analyzed for emboli. The fixed device was snap frozen, sectioned and placed on a slide for histological analysis. Sections were stained immunohistochemically for fibrin and platelet markers.

As described above, six prototypes for each design (3 with tPA and 3 without tPA) were loaded in the flow loop. Emboli entrapment and dissolution was evaluated in three different ways. First, flow measurements were made at different flow rates to determine the degree to which the device retarded flow. Results are outlined in the following table.

TABLE 2

|  | No Device | Media Mesh Only | Prototype Device |
|---|---|---|---|
| 30 ml/min | 30.3 ± 0.6 | 30.0 ± 1.0 | 28.7 ± 0.6 |
| 60 ml/min | 60 ± 0.0 | 59.3 ± 0.6 | 58.3 ± 1.5 |
| 120 ml/min | 119.7 ± 0.6 | 117.3 ± 2.5 | 114.3 ± 2.1 |
| (120 ml/min) | #1 | #2 | #3 |
| Samples w/out tPA | 118 | 116 | 115 |
| tPA | 117 | 115 | 112 |

Second, the PBS was collected. The total collected effluent was passed over a 0.22 μm filter, and the filter was analyzed via light microscopy for presence of emboli. The effluent had no observable emboli after passing through any of the six devices. This demonstrated that the devices were effective to trap the emobli without blocking the flow.

Third, a portion of the embolism protection device was frozen and paraffin embedded for histological archiving. Selected samples were sectioned and prepared for immunohistochemistry as follows. Sections were postfixed for 2 minutes in 100 mmol/L tris-buffered 1% paraformaldehyde containing 1 mmol/L EDTA, pH 7.2, and rinsed with three changes of phosphate buffered saline, pH 7.2. Porcine fibrin decomposition via tPA thrombolysis was detected using murine antibodies specific for neotype beta-chain fibrin (Mouse Anti-Human, Cross-reacts with pig, American Diagnostica, Inc., Greenwich, Conn., Cat 350, 1:100 dilution, rhodamine conjugated, monoclonal IgG-1) and CD41 platelet glycoprotein IIa/IIIb (Mouse Anti-Human, Cross-reacts with pig, DakoCytomation, Carpinteria, Calif., Cat M7057, 1:100 dilution, FITC conjugated, monoclonal IgG-1). The antibodies listed above were diluted in phosphate buffered saline containing 5% bovine serum albumin (Sigma Chemical Co.) and applied to sections for 30 minutes. Then, the section was rinsed with phosphate buffered saline. All sections were cover-slipped with a 1:8 dilution of Vectashield-DAPI (4,6-diamidino-2-phenylindole) in phosphate buffered saline (Vector Laboratories) and evaluated using an epifluorescence microscope.

Stained fibrin was analyzed and scored on a scale of 1-5; 1 being fully intact and 5 being fully dissociated (see sample FIG. 29.). FIGS. 29A and 29B are fibrin recovered from the embolism protection device releasing tPA, while FIGS. 4C and 4D show fibrin at the same magnification recovered from an embolism protection device not releasing tPA. As seen in FIGS. 29A and 29B, fibrin treated with tPA was dissolved away to remove significant portions of the structure and to leave relatively large pores in comparison with the equivalent fibrin in FIGS. 29C and 29D that was not treated with tPA.

The values of the scoring are given in Table 2. Results clearly show degradation of the emboli associated with the device in the treated group and intact emboli in the devices which were not prepared with the tPA. These results show that the tPA eluting from the devices was effective to shrink the emboli.

The embodiments described above are intended to be exemplary and not limiting. Additional embodiments are within the claims. Although the present invention has been described with reference to preferred embodiments, workers skilled in the art will recognize that changes may be made in form and detail without departing from the spirit and scope of the invention.

LITERATURE CITED

All of which are Incorporated by Reference in their Entirety as Well as for the Specific Disclosure Noted 1. Barbut D, Yao F, Lo W, Dilverman R, Hager D N, Trifiletti R R, Gold J P. Determination of size of aortic emboli and embolic loading coronary artery bypass grafting. Ann. Throac. Surg. 1997; 63:1262-7.
2. Barbut D, Caplan L R. Brain complications of cardiac surgery. Curr. Probl. Cardiol. 1997 September; 22(9):449-80.
3. Wolman R L, Nussmeier N A, Aggarwal A, Kanchuger M S, Roach G W, Newman M F, Mangano C M, Marschall K E, Ley C, Boisvert D M, Ozanne G M, Herskowitz A, Graham S H, Mangano D T. Cerebral injury after cardiac surgery: identification of a group at extraordinary risk. Multicenter Study of Perioperative Ischemia Research Group (McSPI) and the Ischemia Research Education Foundation (IREF) Investigators. Stroke 1999. March; 30(3):514-22.
4. Schoen F J. Interventional and Surgical Cardiovascular Pathology. Page 13. W.B. Saunders Company, Philadelphia, Pa. 1989.
5. Llinas R, Barbut D, Caplan L R. Neurologic complications of cardiac surgery. Prog. Cardiovasc. Dis. 2000 September-October; 43(2):101-12.
6. Barbut D, Lo Y W, Gold J P, Trifiletti R R, Yao F S, Hager D N, Hinton R B, Isom O W. Impact of ebolization during coronary artery bypass grafting on outcome and length of stay. Ann. Thorac. Surg. 1997 April; 63(4):998-1002.
7. Bick R L. Hereditary and acquired thrombophilia: preface. Semin. Thromb. Hemost. 1999; 25:251-253.
8. Fasseas P, Orford J L, Denktas A E, Berger P B. Distal protection devices during percutaneous coronary and carotid interventions. Curr. Control Trials Cardiovasc. Med. 2001; 2(6):286-291.
9. Mohammad S F. Enhanced risk of infection with device-associated thrombi. American Society of Artificial Internal Organs J. 2000 November-December; 46(6); S63-8.
10. Allcock H R, Lampe F W. Contemporary Polymer Chemistry. Page 8 Second edition Prentice Hall, Engle Cliffs, N.J., USA 1990.
11. Chapiro, A. Radiation Chemistry of Polymer Systems. Interscience, New York, 1962.
12. Bos G W, Poot A A, Beugeling T, Van Aken W G, Feijen J. Small-diameter vascular graft prostheses: current status. Arch. physiol. Biochem. 1998 April; 106(2):100-15.
13. Chu C, Vonfaunldofer J A, Greisler H P. Wound Closure Biomaterials and Devices. CRC Press New York 1996.
14. Karadag E, Saraydin D, Caldiran Y, Guven O. Swelling studies of copolymeric Acrylamide/crotonic acid hydrogels as carriers for agricultural uses. Polymers for Advanced Technologies 2000 February; 11(2):59-68.
15. Kim S W, Bae Y H, Okano T. Hydrogels: swelling, drug loading, and release. Pharm. Res. 1992 March; 9(3):283-90.
16. Gehrke S H, Andrews G P, Cussler E L. Chemical aspects of gel extraction. Chemical Engineering Science 1986; 41:2153-2160.
17. Trimnell D, Fanta C F. Formulations Prepared from Polyacrylamide and Starch. J. Polym. Mater. 1994; 11:271-277.
18. FDA Document number 02D-074 Denture Cleaners, Adhesives, Cushions, and repair materials:5. Polyacrlamide polymer denture adhesive (21 C.F.R. 872.3480).
19. Reichenspurner H, Navia J A, Berry G, Robbins R C, Barbut D, Gold J P, Reichart B. Particulate emboli capture by an intra-aortic filter device during cardiac surgery. J. Thorac. Cardiovasc. Surg. 2000 February; 119(2):233-41.
20. Harringer W, Capture of particulate emboli during cardiac procedures in which aortic cross-clamp is used. Ann. Thorac. Surg. 2000 February; 119 (2) 701119-23.
21. Verstraete M. The search for the ideal thrombolytic agent. J. Am. Coll. Cardiol. 1987 November; 10 (5 Suppl B):4B-10B.
22. Loscalzo J, Braunwald E. Tissue plasminogen activator. New England J. Med. 1988 Oct. 6; 319 (14):925-31.
23. Verstraete M, Collen D. Pharmacology of thrombolytic drugs. J. Am. College Cardiol. 1986 December; 8(6 Suppl B):33B-40B.
24. Hoyle, C E, Clark D. Polymer, 38, 5698 (1997).
25. Kaetsu, I Radiation synthesis of fabrications of biomedical applications, Radiat. Physics. Chem. 46 (4-6) 1995.
26. Tanaka, T. Phase transitions in gels and single polymers. Polymer 1979 20:1404-1412.
27. Patras G, Qiao G G, Solomon D H. Novel cross-linked homogeneous polyacrylamide gels with improved separation properties: Investigation of the cross-linker Functionality. Electrophoresis 2001, 22, 4303-4310.
28. Mandeville, III, et al., Ionic polymers as anti-infective agents U.S. Pat. No. 6,395,777 May 28, 2002.
29. Pharm. Res. 1989, volume 3, page 368. (See also 20.)
30. Vrachliotis T G, Rabkin D J, Berbaum K, Lang E V. Impact of unilateral common iliac vein occlusion on trapping efficacy of the Greenfield filter: an in vitro study. Acad. Radiol. 2001 June; 8(6):494-500.
31. Wu J H and Diamond S L, Tissue plasminogen activator (tPA) inhibits plasmin degradation of fibrin. A mechanism that slows tPA-mediated fibinolysis but does not require alpha 2-anitplasmin or leakage of intrinsic plasminogen. Journal Clinical Investigation 1995; 95(6):2483-2490.
32. Hrach C J, Johnson M W, Hassan A S, Lei B. Sieving P A and Elner V M, Retinal toxicity of commercial intravitreal tissue plasminogen activator solution in cat eyes. Archive Ophthalmology 2000 May; 118(5)659-63.

What is claimed is:

1. An embolism protection device comprising a delivery tool and a plurality of fibers in a bundle comprising a polymer and having surface capillaries characterized by one or more grooves along the length of the fibers, wherein the fibers are associated with the delivery tool and have a deployed configuration that fills a lumen of a vessel having a diameter corresponding to that of a human vessel in the form of a porous filtration structure forming a fibrous filter mat that blocks a substantial majority of particulates with a diameter between 45 microns to 200 microns while allowing passage of blood cells.

2. The embolism protection device of claim 1 wherein the fibers comprise a hydrophilic polymer.

3. The embolism protection device of claim 1 wherein the fibers comprise polyester.

4. The embolism protection device of claim 1 wherein the fibers comprise a bioresorbable polymer.

5. The embolism protection device of claim 1 wherein the fibers are within a fabric.

6. The embolism protection device of claim 1 wherein the fibers are curled.

7. The embolism protection device of claim 1 wherein the fibers have a curled configuration at body temperature.

8. The embolism protection device of claim 1 wherein the fibers are grafted with a second polymer.

9. The embolism protection device of claim 8 wherein the second polymer is a hydrogel.

10. The embolism protection device of claim 1 further comprising a biocompatible adhesive.

11. A method for trapping emboli, the method comprising placing an embolism protection device of claim 1 within a patient's vessel.

12. The method of claim 11 wherein the placing of the fibers is performed with the delivery tool that associates with the fibers.

13. The method of claim 12 wherein the delivery tool holds the fibers in a configuration for passage through a sheath for deployment of the fibers within the vessel.

14. The method of claim 12 wherein the delivery tool comprises a guidewire.

15. The method of claim 11 wherein the plurality of fibers of the embolism protection device of claim 1 are deployed to the porous filtration structure that fills the lumen of the vessel with an effective pore size to trap a selected range of emboli.

16. The method of claim 11 wherein the fibers are curled at body temperature.

17. The embolism protection device of claim 1 wherein the delivery tool is a guidewire.

18. The embolism protection device of claim 1 wherein the fibers are attached to the delivery tool with an adhesive.

* * * * *